(12) United States Patent
Champion et al.

(10) Patent No.: US 11,859,217 B2
(45) Date of Patent: Jan. 2, 2024

(54) TERMINAL DEOXYNUCLEOTIDYL TRANSFERASE VARIANTS AND USES THEREOF

(71) Applicant: DNA Script, Le Kremlin-Bicêtre (FR)

(72) Inventors: Elise Champion, Paris (FR); Jérôme Loc'h, Le Kremlin-Bicêtre (FR); Mikhael Soskine, Franconville (FR); Elodie Sune, Le Kremlin-Bicêtre (FR)

(73) Assignee: DNA Script, Le Kremlin Bicêtre (FR)

( * ) Notice: Subject to any disclaimer, the term of this patent is extended or adjusted under 35 U.S.C. 154(b) by 38 days.

(21) Appl. No.: 17/293,017

(22) PCT Filed: Nov. 13, 2019

(86) PCT No.: PCT/EP2019/081099
§ 371 (c)(1),
(2) Date: May 11, 2021

(87) PCT Pub. No.: WO2020/099451
PCT Pub. Date: May 22, 2020

(65) Prior Publication Data
US 2022/0002687 A1 Jan. 6, 2022

(30) Foreign Application Priority Data

| Nov. 14, 2018 | (EP) | 18206298 |
| May 28, 2019 | (EP) | 19305677 |
| Sep. 5, 2019 | (EP) | 19195662 |

(51) Int. Cl.
*C12N 9/12* (2006.01)

(52) U.S. Cl.
CPC .... *C12N 9/1264* (2013.01); *C12Y 207/07031* (2013.01)

(58) Field of Classification Search
CPC .................................................. C12N 9/1264
See application file for complete search history.

(56) References Cited

U.S. PATENT DOCUMENTS

| 5,436,143 | A | 7/1995 | Hyman | |
| 5,739,386 | A | 4/1998 | Holmes | |
| 5,763,594 | A | 6/1998 | Hiatt et al. | |
| 5,808,045 | A | 9/1998 | Hiatt et al. | |
| 7,057,026 | B2 | 6/2006 | Barnes et al. | |
| 8,808,988 | B2 | 8/2014 | Zhao et al. | |
| 10,760,063 | B2 * | 9/2020 | Efcavitch | C12Y 207/07031 |
| 10,774,316 | B2 * | 9/2020 | Efcavitch | C12Y 207/07031 |
| 11,390,858 | B2 * | 7/2022 | Tubbs | C12Y 207/07031 |
| 2005/0037991 | A1 | 2/2005 | Veeraiah et al. | |

FOREIGN PATENT DOCUMENTS

| CA | 3024184 | 12/2017 | |
| FR | 3052462 A1 * | 12/2017 | C12N 15/70 |
| WO | 91006678 | 5/1991 | |
| WO | 2004005667 | 1/2004 | |
| WO | 2015159023 | 10/2015 | |
| WO | 2017216472 | 12/2017 | |

OTHER PUBLICATIONS

Becker et al. (1967) "The Enzymatic Cleavage of Phosphate Termini from Polynucleotides*" J. Biol. Chem., 242(5): 936-950.
Bentolila et al. (1995) "The two isoforms of mouse terminal deoxynucleotidyl transferase differ in both the ability to add N regions and subcellular localization" EMBO J., 14(17): 4221-4229.
Boule et al. (1995) "High-level expression of murine terminal deoxynucleotidyl transferase in*Escherichia coli* grown at low temperature and overexpressingargU tRNA" Mol. Biotechnology, 10: 199-208.
Cameron et al. (1977) "3'-Phosphatase activity in T4 polynucleotide kinase" Biochemistry, 16(23): 5120-5126.
Canard et al. (1994) "DNA polymerase fluorescent substrates with reversible 3'-tags" Gene, 148: 1-6.
Canard et al. (1995) "Catalytic editing properties of DNA polymerases" Proc. Natl. Acad. Sci., 92(24):10859-10863.
Corpet (1988) "Multiple sequence alignment with hierarchical clustering" Nucl. Acids Res., 16 (22): 10881-10890.
Delarue et al. (2002) Crystal structures of a template-independent DNA polymerase: murine terminal deoxynucleotidyltransferase The Embo Journal, 21(3): 427-439.
Ferrero et al. (2000) "Chemoenzymatic Transformations in Nucleoside Chemistry" Monatsh. Chem., 131: 585-616.
Grantham (1974) "Amino Acid Difference Formula to Help Explain Protein Evolution" Science, 185(4154): 862-864.
Jensen et al. (2018) "Template-Independent Enzymatic Oligonucleotide Synthesis (TiEOS): Its History, Prospects, and Challenges" Biochemistry, 57: 1821-1832.
Kodumal et al. (2004) "Total synthesis of long DNA sequences: Synthesis of a contiguous 32-kb polyketide synthase gene cluster" Proc. Natl. Acad. Sci., 101: 15573-15578.
Meng et al. "Design and Synthesis of a Photocleavable Fluorescent Nucleotide 3'-O-Allyl-dGTP-PC-Bodipy-FL-510 as a Reversible Terminator for DNA Sequencing by Synthesis" J. Org. Chem., 71: 3248-3252 (2006).

(Continued)

*Primary Examiner* — Yong D Pak
(74) *Attorney, Agent, or Firm* — MORRISON & FOERSTER LLP

(57) ABSTRACT

The present invention is directed to terminal deoxynucleotidyltransferase (TdT) variants that (i) comprise an amino acid sequence that is at least a specified percent identical to an indicated SEQ ID NOs and have at least one substitution at Q455 or at least Q455 plus at least one further substitution at G186, S248, T331, Q390, K394 or H466 (where positions are with respect to SEQ ID NO 1 and functionally equivalent positions in indicated SEQ ID NOs), (ii) are capable of template-free extension of a polynucleotide, and (iii) exhibit enhanced stability or enhanced efficiency in incorporating 3'-O-blocked nucleoside triphosphates into a polynucleotide. The invention is also directed to the use of these TdT variants for synthesizing polynucleotides of any predetermined sequence.

10 Claims, 3 Drawing Sheets

Specification includes a Sequence Listing.

(56) References Cited

OTHER PUBLICATIONS

Metzker et al. (1994) "Termination of DNA synthesis by novel 3'-modifieddeoxyribonucleoside 5'-triphosphates" Nucleic Acids Research, 22(20): 4259-4267.
Rasolonjatovo et al. (1999) "Development of a New DNA Sequencing Method: 3'-Ester Cleavage Catalyzed by Taq DNA Polymerase" Nucleosides & Nucleotides, 18(4-5): 1021-1022.
Schmitz et al. "Solid-Phase Enzymatic Synthesis of Oligonucleotides†" Organic Lett., 1(11): 1729-1731.
Stemmer et al. (1995) "Single-step assembly of a gene and entire plasmid from large numbers of oligodeoxyribonucleotides" Gene, 164: 49-53.
Taunton-Rigby (1973) "Oligonucleotide synthesis. III. Enzymically removable acyl protecting groups" J. Org. Chem., 38(5): 977-985.
Uemura et al. (1989) "Regioselective deprotection of 3',5'-O-acylated pyrimidine nucleosides by lipase and esterase" Tetrahedron Lett., 30(29): 3819-3820.

* cited by examiner

Fig. 2

Table 1

| SEQ ID NO | Supplemental Substitutions | | | | | | | | | | |
|---|---|---|---|---|---|---|---|---|---|---|---|
| | L181F/A/M/Y | M192R/Q | A237V | L260P/R/K | C302G/R | R336L/N | G413L/S | E418A/V | R454P/N/A/V | E457N/L/T/S/K | R480K/E/D |
| 1 | L181F/A/M/Y | M192R/Q | A237V | L260P/R/K | C302G/R | R336L/N | G413L/S | E418A/V | R454P/N/A/V | E457N/L/T/S/K | R480K/E/D |
| 3 | L52F/A/M/Y | M63R/Q | A108V | L131P/R/K | C173G/R | R207L/N | G284L/S | E289A/V | R325P/N/A/V | E328N/L/T/S/K | R351K/E/D |
| 4 | --- | M63R/Q | A110V | L131P/R/K | C173G/R | R207L/N | --- | --- | R324P/N/A/V | E327N/L/T/S/K | R353K/E/D |
| 5 | --- | M63R/Q | A110V | L131P/R/K | C173G/R | R207L/N | --- | E294A/V | R324P/N/A/V | E327N/L/T/S/K | R353K/E/D |
| 6 | --- | --- | A107V | --- | C172G/R | R206L/N | --- | E290A/V | R320P/N/A/V | --- | --- |
| 7 | --- | M63R/Q | A110V | L131P/R/K | C173G/R | R207L/N | --- | E292A/V | R331P/N/A/V | E334N/L/T/S/K | R354K/E/D |
| 8 | --- | M63R/Q | A110V | L131P/R/K | C173G/R | R207L/N | --- | --- | --- | E328N/L/T/S/K | --- |
| 9 | --- | --- | A111V | L132P/R/K | C174G/R | R208L/N | --- | --- | R331P/N/A/V | E334N/L/T/S/K | R354K/E/D |
| 10 | --- | M73R/Q | A110V | L131P/R/K | C173G/R | R207L/N | --- | E295A/V | R325P/N/A/V | E328N/L/T/S/K | --- |
| 11 | --- | M64R/Q | A111V | L132P/R/K | C174G/R | R208L/N | --- | --- | --- | E329N/L/T/S/K | R355K/E/D |
| 12 | --- | M61R/Q | A108V | L129P/R/K | C171G/R | R205L/N | G284L/S | E293A/V | R323P/N/A/V | E326N/L/T/S/K | R352K/E/D |
| 13 | --- | M63R/Q | A110V | L131P/R/K | C173G/R | R207L/N | --- | E298A/V | R329P/N/A/V | E331N/L/T/S/K | --- |
| 14 | --- | --- | A110V | L131P/R/K | C173G/R | R207L/N | --- | E295A/V | R325P/N/A/V | E328N/L/T/S/K | R354K/E/D |
| 15 | --- | M63R/Q | A113V | L134P/R/K | C182G/R | R216L/N | --- | --- | R338P/N/A/V | E341N/L/T/S/K | --- |
| 16 | --- | M65R/Q | A113V | L134P/R/K | C176G/R | R210L/N | --- | E298A/V | R328P/N/A/V | E331N/L/T/S/K | --- |

Fig. 3

Table 2

| SEQ ID NO | | | | | | Stability Substitutions | | | | | |
|---|---|---|---|---|---|---|---|---|---|---|---|
| | Q166E | D170R | C188R | L189D | S223R | G227E | S248A | S275E | Q278R | F322Y | V328M | M330V |
| 1 | Q166E | D170R | C188R | L189D | S223R | G227E | S248A | S275E | Q278R | F322Y | V328M | M330

US 11,859,217 B2

TERMINAL DEOXYNUCLEOTIDYL TRANSFERASE VARIANTS AND USES THEREOF

BACKGROUND

The use of highly purified inexpensive polynucleotides of predetermined sequences in a wide range of lengths has become central to a host of technologies, including genomic and diagnostic sequencing, multiplex nucleic acid amplification, therapeutic antibody development, synthetic biology, nucleic acid-based therapeutics, DNA origami, DNA-based data storage, and the like. Recently, interest has arisen in supplementing or replacing chemically-based synthesis methods by enzymatically-based methods using template-free polymerases, such as, terminal deoxynucleotidyl transferase (TdT), because of the proven efficiency of such enzymes and the benefit of mild non-toxic reaction conditions, e.g. Ybert et al, International patent publication WO2015/159023; Hiatt et al, U.S. Pat. No. 5,763,594; Jensen et al, Biochemistry, 57: 1821-1832 (2018); and the like. Most approaches in enzyme-based synthesis require the use of reversibly blocked nucleoside triphosphates in order to obtain a desired sequence in the polynucleotide product. Unfortunately, natural TdTs incorporate such modified nucleoside triphosphates with greatly reduced efficiency as compared to unmodified nucleoside triphosphates.

In view of the above, the field of template-free enzymatically-based polynucleotide synthesis would be advanced if new template-free polymerases, such as variant TdTs, were available that could incorporate reversibly blocked nucleoside triphosphates with greater efficiency.

SUMMARY OF THE INVENTION

The present invention is directed to terminal deoxynucleotidyl transferase (TdT) variants that display enhanced efficiency in incorporating reversibly blocked nucleoside triphosphates into a polynucleotide, and to their use in synthesizing polynucleotides of any predetermined sequence. Additionally, in some embodiments, TdT variants of the invention exhibit enhanced stability with respect to wildtype enzymes. In part the invention is based on the discovery that the efficiency of TdT-based nucleotide incorporation depends in part on the nucleotide sequence of the 3' end of the polynucleotide being extended; thus, the invention is in part an appreciation and recognition that TdT variants of the invention are capable of efficiently extending a polynucleotide independent of the nucleotide sequence of its 3' end.

In some embodiments, the invention is directed to a terminal deoxynucleotidyl transferase (TdT) variant comprising an amino acid sequence at least sixty percent identical to an amino acid sequence selected from SEQ ID NO: 3, 4, 5, 6, 7, 8, 9, 10, 11, 12, 13, 14, 15 or 16 with a substitution of glutamine at position 326 with respect to SEQ ID NOs 3, 8, 10 and 14, or glutamine at position 325 with respect to SEQ ID NO: 4 and 5, or glutamine at position 332 with respect to SEQ ID NO: 7 and 9, or glutamine at position 329 with respect to SEQ ID NO: 13 and 16, or glutamine at position 321 with respect to SEQ ID NO: 6, or glutamine at position 327 with respect to SEQ ID NO: 11, or glutamine at position 324 with respect to SEQ ID NO: 12, or glutamine at position 339 with respect to SEQ ID NO: 15, or glutamine at position 309 with respect to SEQ ID NO: 24 and 26, or glutamine at position 307 with respect to SEQ ID NO: 25, wherein the TdT variant (i) is capable of synthesizing a nucleic acid fragment without a template and (ii) is capable of incorporating a 3'-O-modified nucleotide onto a free 3'-hydroxyl of a nucleic acid fragment.

In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. In some embodiments, the variant consists in a sequence selected from the group consisting in SEQ ID NO: 3, 4, 5, 6, 7, 8, 9, 10, 11, 12, 13, 14, 15, 16, 24, 25 or 26, with one or more of the disclosed amino acid substitutions. As used herein, the percent identity values used to compare a reference sequence to a variant sequence do not include the expressly specified amino acid positions containing substitutions of the variant sequence; that is, the percent identity relationship is between sequences of a reference protein and sequences of a variant protein outside of the expressly specified positions containing substitutions in the variant. Thus, for example, if the reference sequence and the variant sequence each comprised 100 amino acids and the variant sequence had mutations at positions 25 and 81, then the percent identity would be in regard to sequences 1-24, 26-80 and 82-100.

In regard to (ii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate.

In some embodiments, the above substitution for glutamine is selected from the group consisting of T, F, L and M; in other embodiments, the above substitution for glutamine is selected from the group consisting of T, F, L, M, I, V and Y. In some embodiments, said substitution is F. In some embodiments, the substitution of glutamine may be in combination with other mutations described herein, such as those at the lysine, histidine, alanine, tryptophan, glycine or glutamine below.

In some embodiments, the invention is directed to a terminal deoxynucleotidyl transferase (TdT) variant comprising an amino acid sequence at least sixty percent 60% identical to an amino acid sequence selected from SEQ ID NO: 3, 5, 6, 7, 8, 9, 10, 11, 12, 13, 14, 15 or 16 and comprising a substitution of lysine at position 265 with respect to SEQ ID NOs 3, 7, 8, 9, 10, 13 and 14, or lysine at position 263 with respect to SEQ ID NOs 6 and 12, or lysine at position 264 with respect to SEQ ID NO 5, or lysine at position 266 with respect to SEQ ID NO 11, or lysine at position 268 with respect to SEQ ID NO 16, or lysine at position 272 with respect to SEQ ID NO 15, wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. In regard to (ii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate. In some embodiments, the amino acid substitution of lysine is selected from the group consisting of E, T, A and R. In some embodiments, said substitution is T. In some embodiments, the substitution of lysine may be in combination with other mutations described herein, such as those at the glutamine above, or the histidine, alanine, tryptophan, glycine or glutamine below.

In some embodiments, the invention is directed to a terminal deoxynucleotidyl transferase (TdT) variant comprising an amino acid sequence at least sixty percent 60% identical to an amino acid sequence selected from SEQ ID NO: 3, 4, 5, 6, 7, 8, 9, 10, 11, 12, 13, 14, 15 or 16 and comprising a substitution of histidine at position 337 with respect to SEQ ID NOs 3, 8, 10 and 14, or histidine at position 336 with respect to SEQ ID NOs 4 and 5, or histidine at position 343 with respect to SEQ ID NOs 7 and 9, or histidine at position 340 with respect to SEQ ID NOs 13 and 16, or histidine at position 332 with respect to SEQ ID NO 6, or histidine at position 338 with respect to SEQ ID NO 11, or histidine at position 335 with respect to SEQ ID NO 12, or histidine at position 350 with respect to SEQ ID NO 15, wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. In regard to (ii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate. In some embodiments, the amino acid substitution of histidine is selected from the group consisting of Y, F, N and D. In some embodiments, the substitution of histidine may be in combination with other mutations described herein, such as those at the glutamine or lysine above, or the alanine, tryptophan, glycine or glutamine below.

In some embodiments, the invention is directed to a terminal deoxynucleotidyl transferase (TdT) variant comprising an amino acid sequence at least sixty percent 60% identical to an amino acid sequence selected from SEQ ID NO: 3, 4, 5, 6, 8, 9, 10, 11, 12, 13, 14 or 15 and comprising a substitution of tryptophan at position 377 with respect to SEQ ID NOs 3, 8, 10 and 14, or tryptophan at position 376 with respect to SEQ ID NOs 4 and 5, or tryptophan at position 372 with respect to SEQ ID NO 6, or tryptophan at position 380 with respect to SEQ ID NO 13, or tryptophan at position 383 with respect to SEQ ID NO 9, or tryptophan at position 378 with respect to SEQ ID NO 11, or tryptophan at position 375 with respect to SEQ ID NO 12, or tryptophan at position 380 with respect to SEQ ID NO 13, or tryptophan at position 390 with respect to SEQ ID NO 15, wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. In regard to (ii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate. In some embodiments, tryptophan is substituted with R or K. In some embodiments, tryptophan is substituted with R. In some embodiments, the substitution of tryptophan may be in combination with other mutations described herein, such as those at the glutamine, lysine or histidine above, or the alanine, or glycine, or glutamine below.

In some embodiments, the invention is directed to a terminal deoxynucleotidyl transferase (TdT) variant comprising an amino acid sequence at least sixty percent 60% identical to an amino acid sequence selected from SEQ ID NO: 3, 4, 5, 6, 8, 10, 11, 13, 14, 15 or 16 with a substitution of alanine at position 17 with respect to SEQ ID NOs 3, 4, 5, 6, 8, 10, 13, 14 and 15, or alanine at position 18 with respect to SEQ ID NO: 11 and 16, wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. In regard to (iii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate. In some embodiments, the above substitution for alanine is V, I or L. In some embodiments, the above substitution for alanine is V. In some embodiments, the substitution of alanine may be in combination with other mutations described herein, such as those at the glutamine, lysine, histidine or tryptophan above, or the glycine or glutamine below.

In some embodiments, the invention is directed to a terminal deoxynucleotidyl transferase (TdT) variant comprising an amino acid sequence at least sixty percent 60% identical to an amino acid sequence selected from SEQ ID NO: 3, 9, 11 or 15 with a substitution of glycine at position 57 with respect to SEQ ID NOs 3 and 15, or glycine at position 58 with respect to SEQ ID NO: 9 and 11, wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. In regard to (ii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate. In some embodiments, the above substitution for glycine is E. In some embodiments, the substitution of glycine may be in combination with other mutations described herein, such as those at the glutamine, lysine, histidine, tryptophan or alanine above and/or the glutamine described below.

In some embodiments, the invention is directed to a terminal deoxynucleotidyl transferase (TdT) variant comprising an amino acid sequence at least sixty percent 60% identical to an amino acid sequence selected from SEQ ID NO: 3, 4, or 6 and comprising a substitution of glutamine at position 261 with respect to SEQ ID NO: 3, or glutamine at position 262 with respect to SEQ ID NO: 6, or glutamine at position 264 with respect to SEQ ID NO 4, wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. In regard to (ii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate. In some embodiments, the amino acid substitution of glutamine is R. In some embodiments, the substitution of glutamine at this position may be in combination with other mutations described herein, such as those at the glutamine, histidine, lysine, alanine, tryptophan or glycine above.

In some embodiments, the invention is directed to a terminal deoxynucleotidyl transferase (TdT) variant comprising an amino acid sequence at least ninety percent identical to the amino acid sequence as set forth in SEQ ID NO: 4 with substitutions at position M63, R207, R324 and E327. In some embodiments, the invention is directed to a terminal deoxynucleotidyl transferase (TdT) variant comprising or consisting in an amino acid sequence at least ninety percent identical to the amino acid sequence as set forth in SEQ ID NO: 24 with substitutions at positions M47, R190, R308 and E311. In some embodiments, the invention is directed to a terminal deoxynucleotidyl transferase (TdT) variant comprising or consisting in an amino acid sequence at least ninety percent identical to the amino acid sequence as set forth in SEQ ID NO: 26 with substitutions at positions M46, R190 and E311. In a particular embodiment, at least one of the amino acid substitutions is selected from the group consisting in M46R, M47R, M63R, R190L, R207L, E227N and E311N. In some embodiments, the invention is directed to a terminal deoxynucleotidyl transferase (TdT) variant comprising an amino acid sequence at least ninety percent identical to the amino acid sequence as set forth in SEQ ID NO: 25 with substitutions at positions R184, R306 and E309. Particularly, the substitutions are selected from the group consisting in R184L, R306A and E309N. In an embodiment, the variant consists in an amino acid sequence having at least 90% identity with the amino acid sequence set forth in SEQ ID NO: 25 with the substitutions R184L, R306A and E309N.

In some embodiments, a TdT variant of the invention comprises substitutions of glutamine (first occurrence above), lysine, histidine, tryptophan, alanine, glycine and glutamine (second occurrence above) at the indicated positions and specified SEQ ID NOs described above.

In some embodiments, a TdT variant of the invention comprises an isolated protein.

In addition to the above TdT variants which comprise one or more substitutions of glutamine, lysine, histidine, tryptophan, alanine and/or glycine at the indicated positions of the specified SEQ ID NOs, in some embodiments, each such TdT variant may further comprise from 1 to 11 additional substitutions selected from the positions listed in the rows of Table 1 (set forth in FIG. 2) for the specified SEQ ID NO. Such additional substitutions are sometimes referred to herein as "supplemental substitutions" and contribute to an increased efficiency or rate of incorporation of 3'-O-modified nucleoside triphosphates onto a polynucleotide. In some embodiments, the supplemental substitutions are selected from Table 1. For example, a TdT variant with arginine substituted for glutamine at position 326 of SEQ ID NO 3 (as described above) may further comprise the following substitutions: L52F, M63R, A108V and L131P (that is, substitutions for the first four positions listed in row 2 of Table 1). Thus, in this example, the TdT variant may be characterized as follows using the nomenclature described below: Q326R+L52F+M63R+A108V+L131P with respect to SEQ ID NO: 3, and otherwise comprising at least 90 percent sequence identity with SEQ ID NO 3.

In another example, a TdT variant with arginine substituted for glutamine at position 325 of SEQ ID NO 5, aspartic acid substituted for histidine at position 336 of SEQ ID NO 5, and arginine substituted for tryptophan at position 376 of SEQ ID NO 5, may further comprise the substitutions M63R, A110Y, L131P, C173G, R207N, E294A, R325P, E327N and R353K (selected from row 4 of Table 1, set forth in FIG. 2). Thus, in this example, the TdT variant may be characterized as Q325R+H336D+W376D+M63R+A110V+L131P+C173G+R207N+E294A+R325P+E327N+R353K with respect to SEQ ID NO: 5, and otherwise comprise a specified percent sequence identity, such as at least 90 percent sequence identity, with SEQ ID NO: 5.

In addition to the above TdT variants which comprise one or more substitutions of glutamine, lysine, histidine, tryptophan, alanine and/or glycine at the indicated positions of the specified SEQ ID NOs, and in addition to the Supplemental Substitutions described above, in some embodiments, each such TdT variant may further comprise from 1 to 12 additional substitutions selected from the positions listed in the rows of Table 2 (set forth in FIG. 3) for the specified SEQ ID NO. Such additional substitutions are sometimes referred to herein as "Stability Substitutions" and contribute to an increased stability of a TdT variant, particularly with respect to reaction conditions of template-free enzymatic polynucleotide incorporation, and with respect to elevated temperature. For example, a TdT variant may comprise substitutions A17V, K265E and W377R from Table 3B, supplemental substitutions M63R, L131P, C173G, R207L, G284L and R325P from Table 1, and stability substitutions S119A and S146E from Table 2, wherein the position numbers are with respect to SEQ ID NO: 3. Such TdT variant may be designated as A17V+M63R+S119A+L131P+S146E+C173G+R207L+K265E+G284L+R325P+W377R and it is understood that in addition to these specific substitution the TdT variant comprises a specified percent sequence identity, such as at least 90 percent sequence identity, with SEQ ID NO: 3.

In some embodiments, a TdT variant of the invention comprises all or part of a BRCT-like segment attached to its N-terminus, e.g. see Delarue et al, EMBO J., 21(3): 427-439 (2002).

In some embodiments, the invention is directed to TdT variants comprising an amino acid sequence that has at least 90 percent identity with SEQ ID NO: 1, wherein each such TdT variant (i) comprises at least one mutation at one or more positions selected from the group consisting of G186, S248, T331, Q390, K394, Q455 or H466 with respect to SEQ ID NO: 1, or a functional equivalent thereof, and (ii) is capable of extending a polynucleotide without a template, and (iii) is capable of incorporating 3'-O-modified nucleoside triphosphates with greater efficiency than a wild type TdT. In some embodiments, TdT variants of the invention comprise G186E. In some embodiments, TdT variants of the invention comprise K394 E/T/A/R. In some embodiments, the invention is directed to TdT variants comprising an amino acid sequence that has at least 90 percent identity with SEQ ID NO: 3, wherein each such TdT variant (i) comprises at least one mutation at one or more positions selected from the group consisting of G57, S119, T202, Q261, K265, Q326 or H337 with respect to SEQ ID NO: 3, or a functional equivalent thereof, and (ii) is capable of extending a polynucleotide without a template, and (iii) is capable of incorporating 3'-O-modified nucleoside triphosphates with greater efficiency than a wild type TdT.

In the embodiments of this paragraph, the amino acid position numbers are with respect to SEQ ID NO: 3. In some embodiments, TdT variants of the invention comprise G57E. In some embodiments, TdT variants of the invention comprise K265E/T/A/R. In some embodiments, TdT variants of the invention comprise T202A. In some embodiments, TdT variants of the invention comprise Q326T/F/L/M or Q326T/F/L/M/I/V/Y. In some embodiments, TdT variants of the invention comprise S119A. In some embodiments, TdT variants of the invention comprise Q261R. In some embodiments, TdT variants of the invention comprise H337Y/F/D. In some embodiments, TdT variants of the invention comprise one or more amino acid changes selected from the group consisting of T202A, Q326T/F/L/M or Q326T/F/L/M/I/V/Y/W, S119A, Q261R, H337Y/F/D, G57E and K265E/T/A/R. In some embodiments, TdT variants of the invention comprise K265E/T/A; and in other embodiments comprise both G57E and K265E/T/A. In some embodiments, variant TdTs of the invention have at least 95 percent identity with the reference or wild type TdT sequence SEQ ID NO: 3. In some embodiments, variant TdTs of the invention have at least 98 percent identity with SEQ ID NO: 3. In some embodiments, TdT variants of the invention displaying increase efficiency of incorporation comprise one or more amino acid changes selected from the group consisting of T202A, Q326T/F/L/M or Q326T/F/L/M/I/V/Y, Q261R, H337Y/F/D, G57E and K265E/T/A/R. In some embodiments, TdT variants of the invention displaying enhanced stability comprise the amino acid change S119A. In some embodiments, TdT variants of the invention displaying increased efficiency of incorporation comprise, either individually or in combination, G57E, K265T/E/R/A, Q326T/F/L/M, or H337Y/F/D.

The invention further relates to the use of a TdT variant of the invention for synthesizing a nucleic acid molecule without template by the successive addition of one or more 3'-O-modified nucleotides to a nucleic acid fragment. In some embodiments, such methods comprise the steps of (a) providing an initiator comprising an oligonucleotide having a free 3'-hydroxyl; (b) reacting under enzymatic extension conditions a TdT variant of the invention with the initiator or an extended initiator in the presence of a 3'-O-reversibly blocked nucleoside triphosphate. In some embodiments, such method further includes steps of (c) deblocking the extended initiators to form extended initiators with free 3'-hydroxyls and (d) repeating steps (b) and (c) until a nucleic acid molecule of a predetermined sequence is synthesized.

In further embodiments, the invention includes nucleic acid molecules encoding a variant TdTs described above, expression vectors comprising such nucleic acid molecules, and host cells comprising the aforementioned nucleic acid molecules or the aforementioned expression vectors. In still further embodiments, the invention includes processes for producing a variant TdT of the invention, wherein a host cell is cultivated under culture conditions allowing the expression of the nucleic acid encoding said variant TdT, and wherein the variant TdT is optionally retrieved. The invention also includes kits for performing template-free polynucleotide elongations of any predetermine sequence, wherein the kits include a TdT variant of the invention. Such kits may further comprise 3'-O-blocked deoxyribonucleoside triphosphates (dNTPs) for A, C, G and T for DNA elongation, or 3'-O-blocked ribonucleoside triphosphates (rNTPs) for rA, rC, rG and U for RNA elongation.

The present invention advantageously overcomes problems in the field of template-free enzymatic nucleic acid synthesis related to the efficient incorporation of 3'-O-modified nucleoside triphosphates by providing new TdT variants with a capability of incorporating 3'-0-modified nucleotides with greater efficiency or at a higher rate than wild type TdTs or previously available TdT variants, particularly with respect to incorporation of nucleotides onto polynucleotides that comprise certain 3' nucleotide sequences described herein. In some embodiments, the present invention also advantageously overcomes problems in the above field by providing new TdT variants with increased stability in comparison with wild type TdTs.

BRIEF DESCRIPTION OF THE DRAWINGS

FIG. 2 contains Table 1 listing supplementary substitutions for the various SEQ ID NOs.

FIG. 3 contains Table 2 listing stability substitutions for the various SEQ ID NOs.

DETAILED DESCRIPTION OF THE INVENTION

Figure 1:
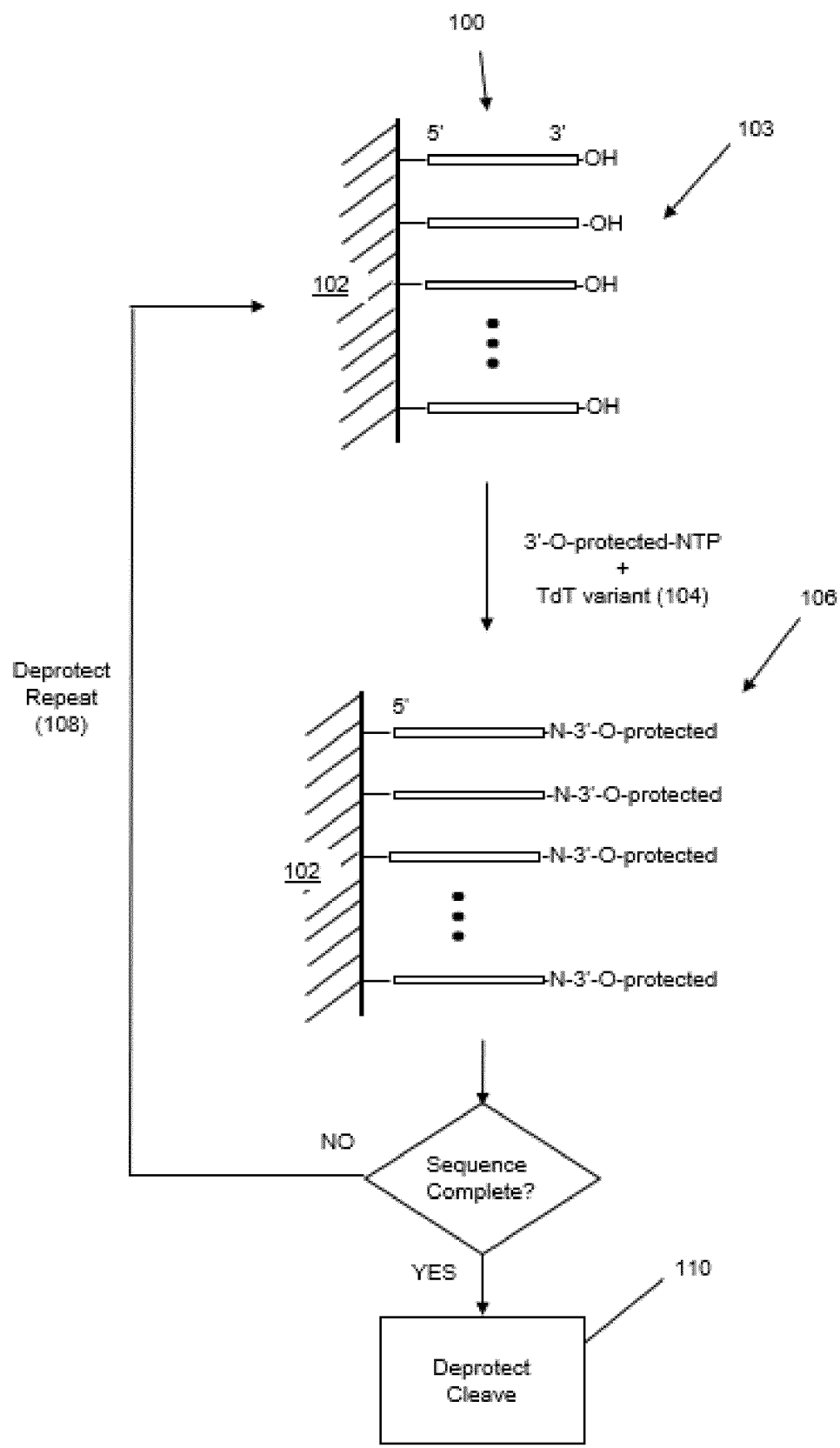
FIG. 1 illustrates diagrammatically the steps of a method of template-free enzymatic nucleic acid synthesis using TdT variants of the invention.

While the invention is amenable to various modifications and alternative forms, specifics thereof have been shown by way of example in the drawings and will be described in detail. It should be understood that the intention is not to limit the invention to the particular embodiments described. It is the intention to cover all modifications, equivalents, and alternatives falling within the spirit and scope of the invention. Guidance for aspects of the invention is found in many available references and treatises well known to those with ordinary skill in the art, including, for example, Sambrook et al. (1989), Molecular cloning: A Laboratory Manual, Cold Spring Harbor Laboratory, and the like.

The present invention provides variants of the TdT polymerase that can be used for synthesizing polynucleotides, such as DNA or RNA, of predetermined sequences without the use of template strand. The TdT variants of the invention allow modified nucleotides, and more particularly 3'-O-reversibly blocked nucleoside triphosphates, to be used in an enzyme-based method of polynucleotide synthesis. The variants of the present invention are described according to their mutations or substitutions at specific residues, whose positions are designated with respect to a specified SEQ ID NO.

In some embodiments, a TdT variant may be operably linked to a linker moiety including a covalent or non-covalent bond; amino acid tag (e.g., poly-amino acid tag, poly-His tag, 6His-tag); chemical compound (e.g., polyethylene glycol); protein-protein binding pair (e.g., biotin-avidin); affinity coupling; capture probes; or any combination of these. The linker moiety can be separate from or part of a TdT variant (e.g., recombinant His-tagged polymerase, such as exemplified by the following pairs of SEQ ID NOs: 19 and 20, 21 and 22, 23 and 24, and 25 and 26). Typically, the linker moiety does not interfere with the nucleotide binding activity, or catalytic activity of the mutant TdT.

In some of the embodiments described above, the efficiency of a variant TdT in incorporating a 3'O-modified nucleoside triphosphate is at least 105 percent that of a previous available TdT wildtype or variant; in other embodiments, the efficiency of a variant TdT in incorporating a 3'O-modified nucleoside triphosphate is at least 110 percent that of a previous available TdT wildtype or variant; in other embodiments, the efficiency of a variant TdT in incorporating a 3'O-modified nucleoside triphosphate is at least 150 percent that of a previous available TdT wildtype or variant.

In some embodiments, a TdT variant of the invention comprises an amino acid sequences at least 60 percent identical to the SEQ ID NOs specified in Table 3A and comprises at least a substitution of glutamine at the position indicated in column 1 for the specified SEQ ID NO. In some embodiments, a TdT variant of the invention comprises an amino acid sequences at least 60 percent identical to the SEQ ID NOs specified in Table 3A and comprises from 1 to 7 substitutions of glutamine, lysine, histidine, tryptophan, alanine or glycine at the positions indicated in columns 1 to 7, respectively, for the specified SEQ ID NOs. In some embodiments, a TdT variant of the invention comprises an amino acid sequences at least 60 percent identical to the SEQ ID NOs specified in Table 3B and comprises at least a substitution of glutamine with one of T, F, L or M at the indicated position for the specified SEQ ID NO. In some embodiments, a TdT variant of the invention comprises an amino acid sequences at least 60 percent identical to the SEQ ID NOs specified in Table 3B and comprises from 1 to 7 substitutions of glutamine with one of T, F, L or M, lysine with one of E, T, A or R, histidine with one of Y, F or D, tryptophan with R, alanine with V or glycine with E at the positions indicated in columns 1 to 7, respectively, for the specified SEQ ID NOs. Where a cell of the Table is blank at a column and specified SEQ ID NO, the amino acid associated with the column is not present in the specified SEQ ID NO so that there is no substitution at that position of the TdT variant.

Each of the TdT variants described in the previous paragraph further (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 80 percent identity with the indicated SEQ ID NOs. In some embodiments, the percent identity value of the previous paragraph is at least 90 percent identity; in some embodiments, such percent identity value is at least 95 percent identity; in some embodiments, such percent identity value is at least 98 percent identity; in some embodiments, such percent identity value is at least 99 percent identity. In some embodiments, the above-mentioned 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate.

TABLE 3A

TdT variants with substitutions at positions Q455, K394, H466, W506, A146, G186 and/or Q390 (with respect to SEQ ID NO: 1) or functionally equivalent positions of the specified SEQ ID NO

| 1 | 2 | 3 | 4 | 5 | 6 | 7 | SEQ ID NO |
|---|---|---|---|---|---|---|---|
| Q455 | K394 | H466 | W506 | A146 | G186 | Q390 | 1 |
| Q326 | K265 | H337 | W377 | A17 | G57 | Q261 | 3 |
| Q325 | — | H336 | W376 | A17 | — | Q264 | 4 |
| Q325 | K264 | H336 | W376 | A17 | — | — | 5 |
| Q321 | K263 | H332 | W372 | A17 | — | Q262 | 6 |
| Q332 | K265 | H343 | — | — | — | — | 7 |
| Q326 | K265 | H337 | W377 | A17 | — | — | 8 |
| Q332 | K265 | H343 | W383 | — | G58 | — | 9 |
| Q326 | K265 | H337 | W377 | A17 | — | — | 10 |
| Q327 | K266 | H338 | W378 | A18 | G58 | — | 11 |
| Q324 | K263 | H335 | W375 | — | — | Q259 | 12 |
| Q329 | K265 | H340 | W380 | A17 | — | — | 13 |
| Q326 | K265 | H337 | W377 | A17 | — | — | 14 |
| Q339 | K272 | H350 | W390 | A17 | G57 | — | 15 |
| Q329 | K268 | H340 | — | A18 | — | — | 16 |

TABLE 3B

TdT variants with indicated substitutions at positions Q455, K394, H466, W506, A146, G186 and/or Q390 (with respect to SEQ ID NO: 1) or functionally equivalent positions of the specified SEQ ID NO

| 1 | 2 | 3 | 4 | 5 | 6 | 7 | SEQ ID NO |
|---|---|---|---|---|---|---|---|
| Q455T/F/L/M | K394E/T/A/R | H466Y/F/D | W506R/K | A146V/I/L | G186E | Q390R | 1 |
| Q326T/F/L/M | K265E/T/A/R | H337Y/F/D | W377R/K | A17V/I/L | G57E | Q261R | 3 |

TABLE 3B-continued

TdT variants with indicated substitutions at positions Q455, K394, H466, W506, A146, G186 and/or Q390 (with respect to SEQ ID NO: 1) or functionally equivalent positions of the specified SEQ ID NO

| 1 | 2 | 3 | 4 | 5 | 6 | 7 | SEQ ID NO |
|---|---|---|---|---|---|---|---|
| Q325T/F/L/M | — | H336Y/F/D | W376R/K | A17V/I/L | — | Q264R | 4 |
| Q325T/F/L/M | K264E/T/A/R | H336Y/F/D | W376R/K | A17V/I/L | — | — | 5 |
| Q321T/F/L/M | K263E/T/A/R | H332Y/F/D | W372R/K | A17V/I/L | — | Q262R | 6 |
| Q332T/F/L/M | K265E/T/A/R | H343Y/F/D | — | — | — | — | 7 |
| Q326T/F/L/M | K265E/T/A/R | H337Y/F/D | W377R/K | A17V/I/L | — | — | 8 |
| Q332T/F/L/M | K265E/T/A/R | H343Y/F/D | W383R/K | — | G58E | — | 9 |
| Q326T/F/L/M | K265E/T/A/R | H337Y/F/D | W377R/K | A17V/I/L | — | — | 10 |
| Q327T/F/L/M | K266E/T/A/R | H338Y/F/D | W378R/K | A18V/I/L | G58E | — | 11 |
| Q324T/F/L/M | K263E/T/A/R | H335Y/F/D | W375R/K | — | — | Q259R | 12 |
| Q329T/F/L/M | K265E/T/A/R | H340Y/F/D | W380R/K | A17V/I/L | — | — | 13 |
| Q326T/F/L/M | K265E/T/A/R | H337Y/F/D | W377R/K | A17V/I/L | — | — | 14 |
| Q339T/F/L/M | K272E/T/A/R | H350Y/F/D | W390R/K | A17V/I/L | G57E | — | 15 |
| Q329T/F/L/M | K268E/T/A/R | H340Y/F/D | — | A18V/I/L | — | — | 16 |

As noted above, in some embodiments, TdT variants of the invention may comprise, in addition to the substitutions set forth in Tables 3A and 3B, one or more Supplementary Substitutions at the positions listed in Table 1 (set forth in FIG. 2) with respect to the specified SEQ ID NOs, and/or one or more stability enhancing substitutions at the positions listed in Table 2 with respect to the specified SEQ ID NOs (set forth in FIG. 3).

In regard to the stability enhancing mutations of Table 2, several adjacent substitutions are believed to exert a stabilizing effect by forming salt bridges between side chains. Thus, the equivalent stabilizing effect of substitutions Q166E and D170R may be obtained by switching the positions of E and R. Accordingly, in addition to the substitutions shown in Table 2, stabilizing substitutions also include the pairs, Q166R with D170E, C188D with L189R, and S275R with Q278E.

Particular TdT variants of the invention, DS1001 to DS1018, are set forth in Table 4. Each of the TdT variants DS1001 through DS1018 comprises an amino acid sequence at least 60 percent identical to SEQ ID NO 3 and comprises the substitutions at the indicated positions. In some embodiments, TdT variants DS1001 through DS1018 comprises an amino acid sequence at least 80 percent identical to SEQ ID NO 3 and comprises the substitutions at the indicated positions; in some embodiments, TdT variants DS1001 through DS1018 comprises an amino acid sequence at least 90 percent identical to SEQ ID NO 3 and comprises the substitutions at the indicated positions; in some embodiments, TdT variants DS1001 through DS1018 comprises an amino acid sequence at least 95 percent identical to SEQ ID NO 3 and comprises the substitutions at the indicated positions; in some embodiments, TdT variants DS1001 through DS1018 comprises an amino acid sequence at least 97 percent identical to SEQ ID NO 3 and comprises the substitutions at the indicated positions; in some embodiments, TdT variants DS1001 through DS1018 comprises an amino acid sequence at least 98 percent identical to SEQ ID NO 3 and comprises the substitutions at the indicated positions; in some embodiments, TdT variants DS1001 through DS1018 comprises an amino acid sequence at least 99 percent identical to SEQ ID NO 3 and comprises the substitutions at the indicated positions.

TABLE 4

Specific TdT Variants of the Invention

| | |
|---|---|
| DS1001 (TH M27) SEQ ID NO: 17 | A17V + L52F + M63R + A108V + C173G + R207L + K265T + G284P + E289V + R325P + E328N + R351K |
| DS1002 (M44) | A17V + Q37E + D41R + L52F + G57E + M63R + S94R + G98E + A108V + S119A + L131R + S146E + Q149R + C173G + R207L + K265T + G284P + E289V + R325P + Q326F + E328N + H337D + R351K + W377R |
| DS1003 | A17V + Q37E + D41R + L52F + G57E + M63R + S94R + G98E + A108V + S146E + Q149R + C173G + F193Y + V199M + M201V + R207L + K265T + G284P + E289V + Q326F + E328N + R351K |
| DS1004 (M45) | A17V + Q37E + D41R + L52F + G57E + M63R + S94R + G98E + A108V + S146E + Q149R + C173G + F193Y + V199M + M201V + R207L + K265T + G284P + E289V + R325A + Q326F + E328N + R351K |
| DS1005 | A17V + Q37E + D41R + L52F + G57E + M63R + S94R + G98E + A108V + S146E + Q149R + C173G + F193Y + V199M + M201V + R207L + K265T + G284P + E289V + Q326F + E328N + R351K |
| DS1006 (M46) | L52F + A108V + R351K + A17V + Q37E + D41R + G57E+ C59R + L60D + M63R + S94R + G98E + S119A + L131R + S146E + Q149R + C173G + R207L + K265T + G284P + E289V + R325A + Q326F + E328N |
| DS1007 (M47) | L52F + A108V + R351K + A17V + Q37E + D41R + G57E + C59R + L60D + M63R + S94R + G98E + K118Q + S119A + L131R + S146E + Q149R + C173G + R207L + K265T + G284P + E289V + R325A + Q326F + E328N + W377R |
| DS1008 | A17V + Q37E + D41R + L52F + G57E + C59R + L60D + M63R + S94R + G98E + A108V + S119A + L131R + S146E + Q149R + C173G + R207L + F259S + Q261L + G284P + E289V + R325A + Q326F + E328N + R351K + W377R |

TABLE 4-continued

Specific TdT Variants of the Invention

| | |
|---|---|
| DS1009 (MS 13-34) SEQ ID NO: 18 | A17V + D41R + L53F + G57E + C59R + L60D + M63R + S94R + G98E + K118Q + S119A + L131R + S146E + Q149R + C173G + R207L + K265T + G284P + E289V + R325A + Q326F + R351K + W377R |
| DS1010 (MS 34-1) SEQ ID NO: 19 | A17V + D41R + L52F + G57E + C59R + L60D + M63R + S94R + G98E + A108V + S119A + L131R + S146E + Q149R + R207L + K265T + G284P + E289V + R325A + Q326F + R351K |
| DS1011 | A17V + D41R + L53F + G57E + C59R + L60D + M63R + S94R + G98E + K118Q + S119A + L131R + S146E + Q149R + C173G + R207L + K265T + G284P + E289V + Q326F + R351K + W377R |
| DS1012 (M48) | A17V + Q37E + D41R + L52F + G57E + C59R + L60D + M63R + S94R + G98E + A108V + S119A + L131R + S146E + Q149R + C173G + R207L + F259S + Q261L, G284P + E289V + R325A + Q326F + E328N + R351K + W377R |
| DS1013 | A17V + Q37E + D41R + L52F + G57E + M63R + S94R + G98E + A108V + S146E + Q149R + C173G + R207L + K265T + G284P + E289V + R325A + Q326F + E328N + R351K |
| DS1014 (M49) | A17V + Q37E + D41R + L52F + G57E + C59R + L60D + M63R + S94R + G98E + A108V + S119A + L131R + S146E + Q149R + C173G + R207L + E257D + F259S + K260R + Q261L + G284P + E289V + R325A + Q326F + E328N + R351K + W377R |
| DS1015 | A17V + Q37E + D41R + L52F + G57E + C59R + L60D + M63R + S94R + G98E + A108V + S119A + L131R + S146E + Q149R + C173G + F193Y + V199M + M201V + R207L + E257D + F259S + K260R + Q261L + G284P + E289V + R325A + Q326F + E328N + R351K + W377R |
| DS1016 (TH c2_5) SEQID NO: 20 | A17V + D41R + L52F + G57E + M63R + S94R + G98E + A108V + S146E + Q149R + C173G + M184T + R207L + K209H + G284L + E289A + R325V + E328K + R351K |
| DS1017 (M27) SEQID NO: 32 | A17V + L52F + G57E + M63R + A108V + C173G + R207L + K265T + G284P + E289V + R325P + E328N + R351K |
| DS1018 (M60) | A17V + L32T + Q37R + D41R + L52F + G57E + C59R + L60D + M63R + S67A + S94R + G98E + A108V + S119A +L131R + S146E + Q149R + V171A + S172E + C173R + V182I + S183E + R207L + K209H + M210K + T211I + E223G + A224P + E228D + Q261L + G284P + E289V + R325A + Q326F + E328N + R351K + D372E |

TdT variants of the invention as described above each comprise an amino acid sequence having a percent sequence identity with a specified SEQ ID NO, subject to the presence of indicated substitutions. In some embodiments, the number and type of sequence differences between a TdT variant of the invention described in this manner and the specified SEQ ID NO may be due to substitutions, deletion and/or insertions, and the amino acids substituted, deleted and/or inserted may comprise any amino acid. In some embodiments, such deletions, substitutions and/or insertions comprise only naturally occurring amino acids. In some embodiments, substitutions comprise only conservative, or synonymous, amino acid changes, as described in Grantham, Science, 185: 862-864 (1974). That is, a substitution of an amino acid can occur only among members of its set of synonymous amino acids. In some embodiments, sets of synonymous amino acids that may be employed are set forth in Table 5A.

TABLE 5A

Synonymous Sets of Amino Acids I

| Amino Acid | Synonymous Set |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Gly, Ala, Thr, Pro, Ser |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Cys, Ser, Thr |
| His | His, Glu, Lys, Gln, Thr, Arg |
| Gln | Gln, Glu, Lys, Asn, His, Thr, Arg |
| Asn | Asn, Gln, Asp, Ser |
| Lys | Lys, Glu, Gln, His, Arg |
| Asp | Asp, Glu, Asn |
| Glu | Glu, Asp, Lys, Asn, Gln, His, Arg |
| Met | Met, Phe, Ile, Val, Leu |
| Trp | Trp |

In some embodiments, sets of synonymous amino acids that may be employed are set forth in Table 5B.

TABLE 5B

Synonymous Sets of Amino Acids II

| Amino Acid | Synonymous Set |
|---|---|
| Ser | Ser |
| Arg | Arg, Lys, His |
| Leu | Ile, Phe, Met, Leu |
| Pro | Ala, Pro |
| Thr | Thr |
| Ala | Pro, Ala |
| Val | Met, Ile Val |
| Gly | Gly |
| Ile | Met, Phe, Val, Leu, Ile |
| Phe | Met, Tyr, Ile, Leu, Phe |
| Tyr | Trp, Met |
| Cys | Cys, Ser |
| His | His, Gln, Arg |
| Gln | Gln, Glu, His |

TABLE 5B-continued

Synonymous Sets of Amino Acids II

| Amino Acid | Synonymous Set |
| --- | --- |
| Asn | Asn, Asp |
| Lys | Lys, Arg |
| Asp | Asp, Asn |
| Glu | Glu, Gln |
| Met | Met, Phe, Ile, Val, Leu |
| Trp | Trp |

Measurement of Nucleotide Incorporation Activity

The efficiency of nucleotide incorporation by variants of the invention may be measured by an extension, or elongation, assay, e.g. as described in Boule et al (cited below); Bentolila et al (cited below); and Hiatt et al, U.S. Pat. No. 5,808,045, the latter of which is incorporated herein by reference. Briefly, in one form of such an assay, a fluorescently labeled oligonucleotide having a free 3'-hydroxyl is reacted under TdT extension conditions with a variant TdT to be tested for a predetermined duration in the presence of a reversibly blocked nucleoside triphosphate, after which the extension reaction is stopped and the amounts of extension products and unextended initiator oligonucleotide are quantified after separation by gel electrophoresis. By such assays, the incorporation efficiency of a variant TdT may be readily compared to the efficiencies of other variants or to that of wild type or reference TdTs, or other polymerases. In some embodiments, a measure of variant TdT efficiency may be a ratio (given as a percentage) of amount of extended product using the variant TdT over the amount of extended product using wild type TdT in an equivalent assay.

In some embodiments, the following particular extension assay may be used to measure incorporation efficiencies of TdTs: Primer used is the following:

```
                                          (SEQ ID NO: 2)
5'-AAAAAAAAAAAAAGGGG-3'
```

The primer has also an ATTO fluorescent dye on the 5' extremity. Representative modified nucleotides used (noted as dNTP in Table 5) include 3'-O-amino-2',3'-dideoxynucleotides-5'-triphosphates (ONH2, Firebird Biosciences), such as 3'-O-amino-2',3'-dideoxyadenosine-5'-triphosphate. For each different variant tested, one tube is used for the reaction. The reagents are added in the tube, starting from water, and then in the order of Table 6. After 30 min at 37° C. the reaction is stopped by addition of formamide (Sigma).

TABLE 6

Extension Activity Assay Reagents

| Reagent | Concentration | Volume |
| --- | --- | --- |
| H$_2$O | — | 12 µL |
| Activity buffer | 10x | 2 µL |
| dNTP | 250 µM | 2 µL |
| Purified enzyme | 20 µM | 2 µL |
| Fluorescent primer | 500 nM | 2 µL |

The Activity buffer comprises, for example, TdT reaction buffer (available from New England Biolabs) supplemented with CoCl$_2$.

The product of the assay is analyzed by conventional polyacrylamide gel electrophoresis. For example, products of the above assay may be analyzed in a 16 percent polyacrylamide denaturing gel (Bio-Rad). Gels are made just before the analysis by pouring polyacrylamide inside glass plates and let it polymerize. The gel inside the glass plates is mounted on an adapted tank filed with TBE buffer (Sigma) for the electrophoresis step. The samples to be analyzed are loaded on the top of the gel. A voltage of 500 to 2,000V is applied between the top and bottom of the gel for 3 to 6 h at room temperature. After separation, gel fluorescence is scanned using, for example, a Typhoon scanner (GE Life Sciences). The gel image is analyzed using ImageJ software (imagej.nih.gov/ij/), or its equivalent, to calculate the percentage of incorporation of the modified nucleotides.

Hairpin completion assay. In one aspect, the invention includes methods of measuring the capability of a polymerase, such as a TdT variant, to incorporate a dNTP onto a 3' end of a polynucleotide (i.e. a "test polynucleotide"). One such method comprises providing a test polynucleotide with a free 3' hydroxyl under reaction conditions in which it is substantially only single stranded, but that upon extension with a polymerase, such as a TdT variant, forms a stable hairpin structure comprising a single stranded loop and a double stranded stem, thereby allowing detection of an extension of the 3' end by the presence of the double stranded polynucleotide. The double stranded structure may be detected in a variety of ways including, but not limited to, fluorescent dyes that preferentially fluoresce upon intercalation into the double stranded structure, fluorescent resonance energy transfer (FRET) between an acceptor (or donor) on the extended polynucleotide and a donor (or acceptor) on an oligonucleotide that forms a triplex with the newly formed hairpin stem, FRET acceptors and donors that are both attached to the test polynucleotide and that are brought into FRET proximity upon formation of a hairpin, or the like. In some embodiments, a stem portion of a test polynucleotide after extension by a single nucleotide is in the range of 4 to 6 basepairs in length; in other embodiments, such stem portion is 4 to 5 basepairs in length; and in still other embodiments, such stem portion is 4 basepairs in length. In some embodiments, a test polynucleotide has a length in the range of from 10 to 20 nucleotides; in other embodiments, a test polynucleotide has a length in the range of from 12 to 15 nucleotides. In some embodiments, it is advantageous or convenient to extend the test polynucleotide with a nucleotide that maximizes the difference between the melting temperatures of the stem without extension and the stem with extension; thus, in some embodiments, a test polynucleotide is extended with a dC or dG (and accordingly the test polynucleotide is selected to have an appropriate complementary nucleotide for stem formation).

Exemplary test polynucleotides for hairpin completion assays include p875 (5'-CAGTTAAAAACT) (SEQ ID NO: 21) which is completed by extending with a dGTP; p876 (5'-GAGTTAAAACT) (SEQ ID NO: 22) which is completed by extending with a dCTP; and p877 (5'-CAGCAAGGCT) (SEQ ID NO: 23) which is completed by extending with a dGTP. Exemplary reaction conditions for such test polynucleotides may comprise: 2.5-5 µM of test polynucleotide, 1:4000 dilution of GelRed® (intercalating dye from Biotium, Inc., Fremont, CA), 200 mM Cacodylate KOH pH 6.8, 1 mM CoCl$_2$, 0-20% of DMSO and 3' ONH2 dGTP and TdT at desired concentrations. Completion of the hairpin may be monitored by an increase in fluorescence of GelRed® dye using a conventional fluorimeter, such as a TECAN reader at a reaction temperature of 28-38° C., using an excitation filter set to 360 nm and anemission filter set to 635 nm.

In some embodiments of this aspect of the invention, TdT variants may be tested for their capacity for template-free incorporate of nucleoside triphosphates by the following steps: (a) combining a test polynucleotide having a free 3'-hydroxyl, a TdT variant and a nucleoside triphosphate under conditions wherein the test polynucleotide is single stranded but upon incorporation of the nucleoside triphosphate forms a hairpin having a double stranded stem region, and (b) detecting the amount of double stranded stem regions formed as a measure of the capacity of the TdT variant to incorporate the nucleoside triphosphate. In some embodiments, the nucleoside triphosphate is a 3'-O-blocked nucleoside triphosphate.

Measurement of Enzyme Stability

In some embodiments, enzyme stability means a capability of an enzyme (or variant thereof) to retain a particular activity after it has been subjected to destabilizing conditions for a period of time, such as, elevated temperature, lowered temperature, low pH, high pH, exposure to a chaotropic agent, or the like. In some embodiments, enzyme stability may be measured by exposing the enzyme to elevated temperatures, e.g. in the range of 50–70° C. for a period of time, e.g. in the range of 15-30 minutes, after which the activity of template-free elongation of an initiator stranded using a 3'-modified NTP is tested. In other embodiments, enzyme stability may be measured by exposing the enzyme to low pH, e.g. pH in the range of 1-4, for a period of time, e.g. in the range of 15-30 minutes. In some embodiments, TdT variants of the invention having enhanced stability with respect to elevated temperature display template-free initiator elongation activity using 3'-O-modified dNTPs equal to or greater than that of wild type TdT. In some embodiments, TdT variants of the invention having enhanced stability with respect to pH display template-free initiator elongation activity using 3'-O-modified dNTPs equal to or greater than that of wild type TdT. In some embodiments, such elevated temperature or pH stability is with respect to template-free initiator elongation activity using 3'-O-amine protected dNTPs.

Template-Free Enzymatic Synthesis

Template-free enzymatic synthesis of polynucleotides may be carried out by a variety of known protocols using template-free polymerases, such as terminal deoxynucleotidyl transferase (TdT), including variants thereof engineered to have improved characteristics, such as greater temperature stability or greater efficiency in the incorporation of 3'-O-blocked deoxynucleoside triphosphates (3'-O-blocked dNTPs), e.g. Ybert et al, International patent publication WO/2015/159023; Ybert et al, International patent publication WO/2017/216472; Hyman, U.S. Pat. No. 5,436,143; Hiatt et al, U.S. Pat. No. 5,763,594; Jensen et al, Biochemistry, 57: 1821-1832 (2018); Mathews et al, Organic & Biomolecular Chemistry, DOI: 0.1039/c6ob01371f (2016); Schmitz et al, Organic Lett., 1(11): 1729-1731 (1999).

In some embodiments, the method of enzymatic DNA synthesis comprises repeated cycles of steps, such as are illustrated in FIG. 1, in which a predetermined nucleotide is added in each cycle. Initiator polynucleotides (100) are provided, for example, attached to solid support (102), which have free 3'-hydroxyl groups (103). To the initiator polynucleotides (100) (or elongated initiator polynucleotides in subsequent cycles) are added a 3'-O-protected-dNTP and a TdT variant under conditions (104) effective for the enzymatic incorporation of the 3'-O-protected-dNTP onto the 3' end of the initiator polynucleotides (100) (or elongated initiator polynucleotides). This reaction produces elongated initiator polynucleotides whose 3'-hydroxyls are protected (106). If the elongated initiator polynucleotide contains a competed sequence, then the 3'-O-protection group is removed, or deprotected, and the desired sequence is cleaved from the original initiator polynucleotide. Such cleavage may be carried out using any of a variety of single strand cleavage techniques, for example, by inserting a cleavable nucleotide or cleavable linker at a predetermined location within the original initiator polynucleotide. Exemplary cleavable nucleotides or linkers include, but are not limited to, (i) a uracil nucleotide which is cleaved by uracil DNA glycosylase; (ii) a photocleavable group, such as a nitrobenzyl linker, as described in U.S. Pat. No. 5,739,386; or an inosine which is cleaved by endonuclease V. In some embodiments, a cleaved polynucleotide may have a free 5'-hydroxyl; in other embodiments, a cleaved polynucleotide may have a 5'-phosphorylated end. If the elongated initiator polynucleotide does not contain a completed sequence, then the 3'-O-protection groups are removed to expose free 3'-hydroxyls (103) and the elongated initiator polynucleotides are subjected to another cycle of nucleotide addition and deprotection.

In some embodiments, an ordered sequence of nucleotides is coupled to an initiator nucleic acid using a TdT in the presence of 3'-O-reversibly blocked dNTPs in each synthesis step. In some embodiments, the method of synthesizing an oligonucleotide comprises the steps of (a) providing an initiator having a free 3'-hydroxyl; (b) reacting under extension conditions the initiator or an extension intermediate having a free 3'-hydroxyl with a TdT in the presence of a 3'-O-blocked nucleoside triphosphate to produce a 3'-O-blocked extension intermediate; (c) deblocking the extension intermediate to produce an extension intermediate with a free 3'-hydroxyl; and (d) repeating steps (b) and (c) until the polynucleotide is synthesized. (Sometime "an extension intermediate" is also referred to as an "elongation fragment."). In some embodiments, an initiator is provided as an oligonucleotide attached to a solid support, e.g. by its 5' end. The above method may also include washing steps after the reaction, or extension, step, as well as after the de-blocking step. For example, the step of reacting may include a sub-step of removing unincorporated nucleoside triphosphates, e.g. by washing, after a predetermined incubation period, or reaction time. Such predetermined incubation periods or reaction times may be a few seconds, e.g. 30 sec, to several minutes, e.g. 30 min.

The above method may also include capping step(s) as well as washing steps after the reacting, or extending, step, as well as after the deblocking step. As mentioned above, in some embodiments, capping steps may be included in which non-extended free 3'-hydroxyls are reacted with compounds that prevents any further extensions of the capped strand. In some embodiments, such compound may be a dideoxynucleoside triphosphate. In other embodiments, non-extended strands with free 3'-hydroxyls may be degraded by treating them with a 3'-exonuclease activity, e.g. Exo I. For example, see Hyman, U.S. Pat. No. 5,436,143. Likewise, in some embodiments, strands that fail to be deblocked may be treated to either remove the strand or render it inert to further extensions.

In some embodiments that comprise serial synthesis of oligonucleotides, capping steps may be undesirable as capping may prevent the production of equal molar amounts of a plurality of oligonucleotides. Without capping, sequences will have a uniform distribution of deletion errors, but each of a plurality of oligonucleotides will be present in equal molar amounts. This would not be the case where non-extended fragments are capped.

In some embodiments, reaction conditions for an extension or elongation step may comprising the following: 2.0 µM purified TdT; 125-600 µM 3'-O-blocked dNTP (e.g. 3'-O—NH$_2$-blocked dNTP); about 10 to about 500 mM potassium cacodylate buffer (pH between 6.5 and 7.5) and from about 0.01 to about 10 mM of a divalent cation (e.g. CoCl$_2$ or MnCl$_2$), where the elongation reaction may be carried out in a 50 µL reaction volume, at a temperature within the range RT to 45° C., for 3 minutes. In embodiments, in which the 3'-O-blocked dNTPs are 3'-O—NH$_2$-blocked dNTPs, reaction conditions for a deblocking step may comprise the following: 700 mM NaNO$_2$; 1 M sodium acetate (adjusted with acetic acid to pH in the range of 4.8-6.5), where the deblocking reaction may be carried out in a 50 µL volume, at a temperature within the range of RT to 45° C. for 30 seconds to several minutes.

Depending on particular applications, the steps of deblocking and/or cleaving may include a variety of chemical or physical conditions, e.g. light, heat, pH, presence of specific reagents, such as enzymes, which are able to cleave a specified chemical bond. Guidance in selecting 3'-O-blocking groups and corresponding de-blocking conditions may be found in the following references, which are incorporated by reference: U.S. Pat. Nos. 5,808,045; 8,808,988; International patent publication WO91/06678; and references cited below. In some embodiments, the cleaving agent (also sometimes referred to as a de-blocking reagent or agent) is a chemical cleaving agent, such as, for example, dithiothreitol (DTT). In alternative embodiments, a cleaving agent may be an enzymatic cleaving agent, such as, for example, a phosphatase, which may cleave a 3'-phosphate blocking group. It will be understood by the person skilled in the art that the selection of deblocking agent depends on the type of 3'-nucleotide blocking group used, whether one or multiple blocking groups are being used, whether initiators are attached to living cells or organisms or to solid supports, and the like, that necessitate mild treatment. For example, a phosphine, such as tris(2-carboxyethyl)phosphine (TCEP) can be used to cleave a 3'O-azidomethyl groups, palladium complexes can be used to cleave a 3'O-allyl groups, or sodium nitrite can be used to cleave a 3'O-amino group. In particular embodiments, the cleaving reaction involves TCEP, a palladium complex or sodium nitrite.

As noted above, in some embodiments it is desirable to employ two or more blocking groups that may be removed using orthogonal de-blocking conditions. The following exemplary pairs of blocking groups may be used in parallel synthesis embodiments, such as those described above. It is understood that other blocking group pairs, or groups containing more than two, may be available for use in these embodiments of the invention.

| | |
|---|---|
| 3'-O—NH2 | 3'-O-azidomethyl |
| 3'-O—NH2 | 3'-O-allyl |
| 3'-O—NH2 | 3'-O-phosphate |
| 3'-O-azidomethyl | 3'-O-allyl |
| 3'-O-azidomethyl | 3'-O-phosphate |
| 3'-O-allyl | 3'-O-phosphate |

Synthesizing oligonucleotides on living cells requires mild deblocking, or deprotection, conditions, that is, conditions that do not disrupt cellular membranes, denature proteins, interfere with key cellular functions, or the like. In some embodiments, deprotection conditions are within a range of physiological conditions compatible with cell survival. In such embodiments, enzymatic deprotection is desirable because it may be carried out under physiological conditions. In some embodiments specific enzymatically removable blocking groups are associated with specific enzymes for their removal. For example, ester- or acyl-based blocking groups may be removed with an esterase, such as acetylesterase, or like enzyme, and a phosphate blocking group may be removed with a 3' phosphatase, such as T4 polynucleotide kinase. By way of example, 3'-O-phosphates may be removed by treatment with as solution of 100 mM Tris-HCl (pH 6.5) 10 mM MgCl$_2$, 5 mM 2-mercaptoethanol, and one Unit T4 polynucleotide kinase. The reaction proceeds for one minute at a temperature of 37° C.

A "3'-phosphate-blocked" or "3'-phosphate-protected" nucleotide refers to nucleotides in which the hydroxyl group at the 3'-position is blocked by the presence of a phosphate containing moiety. Examples of 3'-phosphate-blocked nucleotides in accordance with the invention arc nucleotidyl-3'-phosphate monoester/nucleotidyl-2',3'-cyclic phosphate, nucicotidyl-2'-phosphate monoester and nucleotidyl-2' or 3'-alkylphosphate diester, and nucleotidyl-2' or 3'-pyrophosphate. Thiophosphate or other analogs of such compounds can also be used, provided that the substitution does not prevent dephosphorylation resulting in a free 3'-OH by a phosphatase.

Further examples of synthesis and enzymatic deprotection of 3'-O-ester-protected dNTPs or 3'-O-phosphate-protected dNTPs are described in the following references: Canard et al, Proc. Natl. Acad. Sci., 92:10859-10863 (1995); Canard et al, Gene, 148: 1-6 (1994); Cameron et al, Biochemistry, 16(23): 5120-5126 (1977); Rasolonjatovo et al, Nucleosides & Nucleotides, 18(4&5): 1021-1022 (1999); Ferrero et al, Monatshefte für Chemie, 131: 585-616 (2000); Taunton-Rigby et al, J. Org. Chem., 38(5): 977-985 (1973); Uemura et al, Tetrahedron Lett., 30(29): 3819-3820 (1989); Becker et al, J. Biol. Chem., 242(5): 936-950 (1967); Tsien, International patent publication WO1991/006678.

As used herein, an "initiator" (or equivalent terms, such as, "initiating fragment," "initiator nucleic acid," "initiator oligonucleotide," or the like) refers to a short oligonucleotide sequence with a free 3'-end, which can be further elongated by a template-free polymerase, such as TdT. In one embodiment, the initiating fragment is a DNA initiating fragment. In an alternative embodiment, the initiating fragment is an RNA initiating fragment. In one embodiment, the initiating fragment possesses between 3 and 100 nucleotides, in particular between 3 and 20 nucleotides. In one embodiment, the initiating fragment is single-stranded. In an alternative embodiment, the initiating fragment is double-stranded. In a particular embodiment, an initiator oligonucleotide synthesized with a 5'-primary amine may be covalently linked to magnetic beads using the manufacturer's protocol. Likewise, an initiator oligonucleotide synthesized with a 3'-primary amine may be covalently linked to magnetic beads using the manufacturer's protocol. A variety of other attachment chemistries amenable for use with embodiments of the invention are well-known in the art, e.g. Integrated DNA Technologies brochure, "Strategies for Attaching Oligonucleotides to Solid Supports," v.6 (2014); Hermanson, Bioconjugate Techniques, Second Edition (Academic Press, 2008); and like references.

Many of the 3'-O-blocked dNTPs employed in the invention may be purchased from commercial vendors or synthesized using published techniques, e.g. U.S. Pat. No. 7,057, 026; International patent publications WO2004/005667, WO91/06678; Canard et al, Gene (cited above); Metzker et al, Nucleic Acids Research, 22: 4259-4267 (1994); Meng et al, J. Org. Chem., 14: 3248-3252 (3006); U.S. patent publication 2005/037991. In some embodiments, the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure:

wherein —Z is any of —C(R')$_2$—O—R", —C(R')$_2$—N(R")$_2$, —C(R')$_2$—N(H)R", —C(R')$_2$—S—R" and —C(R')$_2$—F, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; with the proviso that in some embodiments such substituents have up to 10 carbon atoms and/or up to 5 oxygen or nitrogen heteroatoms; or (R')$_2$ represents a group of formula =C(R''')$_2$ wherein each R''' may be the same or different and is selected from the group comprising hydrogen and halogen atoms and alkyl groups, with the proviso that in some embodiments the alkyl of each R''' has from 1 to 3 carbon atoms; and wherein the molecule may be reacted to yield an intermediate in which each R" is exchanged for H or, where Z is —(R')$_2$—F, the F is exchanged for OH, SH or NH$_2$, preferably OH, which intermediate dissociates under aqueous conditions to afford a molecule with a free 3'-OH; with the proviso that where Z is —C(R')$_2$—S—R", both R' groups are not H. In certain embodiments, R' of the modified nucleotide or nucleoside is an alkyl or substituted alkyl, with the proviso that such alkyl or substituted alkyl has from 1 to 10 carbon atoms and from 0 to 4 oxygen or nitrogen heteroatoms. In certain embodiments, —Z of the modified nucleotide or nucleoside is of formula —C(R')$_2$—N3. In certain embodiments, Z is an azidomethyl group.

In some embodiments, Z is a cleavable organic moiety with or without heteroatoms having a molecular weight of 200 or less. In other embodiments, Z is a cleavable organic moiety with or without heteroatoms having a molecular weight of 100 or less. In other embodiments, Z is a cleavable organic moiety with or without heteroatoms having a molecular weight of 50 or less. In some embodiments, Z is an enzymatically cleavable organic moiety with or without heteroatoms having a molecular weight of 200 or less. In other embodiments, Z is an enzymatically cleavable organic moiety with or without heteroatoms having a molecular weight of 100 or less. In other embodiments, Z is an enzymatically cleavable organic moiety with or without heteroatoms having a molecular weight of 50 or less. In other embodiments, Z is an enzymatically cleavable ester group having a molecular weight of 200 or less. In other embodiments, Z is a phosphate group removable by a 3'-phosphatase. In some embodiments, one or more of the following 3'-phosphatases may be used with the manufacturer's recommended protocols: T4 polynucleotide kinase, calf intestinal alkaline phosphatase, recombinant shrimp alkaline phosphatase (e.g. available from New England Biolabs, Beverly, MA)

In a further particular embodiment, the 3'-blocked nucleotide triphosphate is blocked by either a 3'-O-azidomethyl, 3'-O—NH$_2$ or 3'-O-allyl group.

In still other embodiments, 3'-blocking groups of the invention include 3'-O-methyl, 3'-O-(2-nitrobenzyl), 3'-O-allyl, 3'-O-amine, 3'-O-azidomethyl, 3'-O-tert-butoxy ethoxy, 3'-O-(2-cyanoethyl), and 3'-O-propargyl.

Production of Variant TdTs

Variants of the invention may be produced by mutating known reference or wild type TdT-coding polynucleotides, then expressing it using conventional molecular biology techniques. For example, the mouse TdT gene (SEQ ID NO: 1) may be assembled from synthetic fragments using conventional molecular biology techniques, e.g. using protocols described by Stemmer et al, Gene, 164: 49-53 (1995); Kodumal et al, Proc. Natl. Acad. Sci., 101: 15573-15578 (2004); or the like, or it may be directly cloned from mouse cells using protocols described by Boule et al, Mol. Biotechnology, 10: 199-208 (1998), or Bentolila et al, EMBO J., 14: 4221-4229 (1995); or the like.

For example, an isolated TdT gene may be inserted into an expression vector, such as pET32 (Novagen) to give a vector pCTdT which then may be used to make and express variant TdT proteins using conventional protocols. Vectors with the correct sequence may be transformed in *E. coli* producer strains.

Transformed strains are cultured using conventional techniques to pellets from which TdT protein is extracted. For example, previously prepared pellets are thawed in 30 to 37° C. water bath. Once fully thawed, pellets are resuspended in lysis buffer composed of 50 mM tris-HCL (Sigma) pH 7.5, 150 mM NaCl (Sigma), 0.5 mM mercaptoethanol (Sigma), 5% glycerol (Sigma), 20 mM imidazole (Sigma) and 1 tab for 100 mL of protease cocktail inhibitor (Thermofisher). Careful resuspension is carried out in order to avoid premature lysis and remaining of aggregates. Resuspended cells are lysed through several cycles of French press, until full color homogeneity is obtained. Usual pressure used is 14,000 psi. Lysate is then centrifuged for 1 h to 1h30 at 10,000 rpm. Centrifugate is pass through a 0.2 μm filter to remove any debris before column purification.

TdT protein may be purified from the centrifugate in a one-step affinity procedure. For example, Ni-NTA affinity column (GE Healthcare) is used to bind the polymerases. Initially the column has been washed and equilibrated with 15 column volumes of 50 mM tris-HCL (Sigma) pH 7.5, 150 mM NaCl (Sigma) and 20 mM imidazole (Sigma). Polymerases are bound to the column after equilibration. Then a washing buffer, composed of 50 mM tris-HCL (Sigma) pH 7.5, 500 mM NaCl (Sigma) and 20 mM imidazole (Sigma), is applied to the column for 15 column volumes. After wash the polymerases are eluted with 50 mM tris-HCL (Sigma) pH 7.5, 500 mM NaCl (Sigma) and 0.5M imidazole (Sigma). Fractions corresponding to the highest concentration of polymerases of interest are collected and pooled in a single sample. The pooled fractions are dialyzed against the dialysis buffer (20 mM Tris-HCl, pH 6.8, 200 mM Na Cl, 50 mM MgOAc, 100 mM [NH4]2SO4). The dialysate is subsequently concentrated with the help of concentration filters (Amicon Ultra-30, Merk Millipore). Concentrated enzyme is distributed in small aliquots, 50% glycerol final is added, and those aliquots are then frozen at −20° C. and stored for long term. 5 μL of various fraction of the purified enzymes are analyzed in SDSPAGE gels.

Kits for Practicing Methods of the Invention

The invention includes a variety of kits for practicing methods of the invention. In one aspect, kits of the invention comprise a TdT variant of the invention in a formulation suitable for carrying out template-free enzymatic polynucleotide synthesis as described herein. Such kits may also include synthesis buffers that provide reaction conditions for optimizing the template-free addition or incorporation of a 3'-O-protected dNTP to a growing strand. In some embodiments, kits of the invention further include 3'-O-reversibly protected dNTPs. In such embodiments, the 3'-O-reversibly protected dNTPs may comprise 3'-O-amino-dNTPs or 3'-O-azidomethyl-dNTPs. In further embodiments, kits may include one or more of the following items, either separately or together with the above-mentioned items: (i) deprotection reagents for carrying out a deprotecting step as described herein, (ii) solid supports with initiators attached thereto, (iii) cleavage reagents for releasing completed polynucleotides from solid supports, (iv) wash reagents or buffers for removing unreacted 3'-O-protected dNTPs at the end of an enzymatic addition or coupling step, and (v) post-synthesis processing reagents, such as purification columns, desalting reagents, eluting reagents, and the like.

In regard to items (ii) and (iii) above, certain initiators and cleavage reagents go together. For example, an initiator comprising an inosine cleavable nucleotide may come with an endonuclease V cleavage reagent; an initiator comprising a nitrobenzyl photocleavable linker may come with a suitable light source for cleaving the photocleavable linker; an initiator comprising a uracil may come with a uracil DNA glycosylase cleavage reagent; and the like.

Example 1: Generation, Expression and Purification of TdT Variants

Expression strain generation. The TdT mouse gene may be generated from the pET28 plasmid described in [Boulé et al., 1998, Mol. Biotechnol. 10, 199-208]. For example, the gene may be amplified by using the following primers:

```
T7-pro:
                              (SEQ ID No. 33)
TAATACGACTCACTATAGGG

T7-ter:
                              (SEQ ID No. 34)
GCTAGTTATTGCTCAGCGG
``` through standard molecular biology techniques. The sequence is then cloned into plasmid pET32 backbone to give the new pCTdT plasmid. After sequencing pCTdT is transformed into commercial *E. coli* cells, BL21 (DE3, from Novagen). Growing colonies on plate with kanamycin are isolated and named Ec-CTdT.Polymerase variants generation. The pCTdT vector is used as starting vector. Specific primers comprising one or several point mutations have been generated from Agilent online software (http://www.genomics.agilent.com:80/primerDesignProgram.jsp). The commercially available kit QuickChange II (Agilent) may be used to generate the desired modified polymerase comprising the targeted mutations. Experimental procedure follows the supplier's protocol. After generation of the different vectors, each of them is sequenced. Vectors with the correct sequence are transformed in *E. coli* producer strains. Clones able to grow on kanamycin LB-agar plates are isolated.

Expression. The Ec-CTdT and Ec-DSi or Ec-DSi' strains may be used for inoculating 250 mL erlens with 50 mL of LB media supplemented with appropriate amount of kanamycin. After overnight growth at 37° C., appropriate volumes of these pre-cultures are used to inoculate 5 L erlens with 2 L LB media with kanamycin. The initial OD for the 5 L cultures is chosen to be 0.01. The erlens are put at 37° C. under strong agitation and the OD of the different cultures are regularly checked. After reaching an OD comprised between 0.6 and 0.9 each erlen is supplemented by the addition of 1 mL of 1M IPTG (Isopropyl β-D-1-thiogalactopyranoside, Sigma). The erlens are put back to agitation under a controlled temperature of 37° C. After overnight expression, the cells are harvested in several pellets. Pellets expressing the same variants are pooled and stored at −20° C., eventually for several months.

Extraction. Previously prepared pellets are thawed in 30 to 37° C. water bath. Once fully thawed, pellets are resuspended in lysis buffer composed of 50 mM tris-HCL (Sigma) pH 7.5, 150 mM NaCl (Sigma), 0.5 mM mercaptoethanol (Sigma), 5% glycerol (Sigma), 20 mM imidazole (Sigma) and 1 tab for 100 mL of protease cocktail inhibitor (Thermofisher). Careful resuspension is carried out in order to avoid premature lysis and remaining of aggregates. Resuspended cells are lysed through several cycles of French press, until full color homogeneity is obtained. Usual pressure used is 14,000 psi. Lysate is then centrifuged for 1 h to 1h30 at 10,000 rpm. Centrifugate is pass through a 0.2 µm filter to remove any debris before column purification.

Purification. A one-step affinity procedure is used to purify the produced and extracted polymerase enzymes. A Ni-NTA affinity column (GE Healthcare) is used to bind the polymerases. Initially the column has been washed and equilibrated with 15 column volumes of 50 mM tris-HCL (Sigma) pH 7.5, 150 mM NaCl (Sigma) and 20 mM imidazole (Sigma). Polymerases are bound to the column after equilibration. Then a washing buffer, composed of 50 mM tris-HCL (Sigma) pH 7.5, 500 mM NaCl (Sigma) and 20 mM imidazole (Sigma), is applied to the column for 15 column volumes. After wash the polymerases are eluted with 50 mM tris-HCL (Sigma) pH 7.5, 500 mM NaCl (Sigma) and 0.5M imidazole (Sigma). Fractions corresponding to the highest concentration of polymerases of interest are collected and pooled in a single sample. The pooled fractions are dialyzed against the dialysis buffer (20 mM Tris-HCl, pH 6.8, 200 mM Na Cl, 50 mM MgOAc, 100 mM $[NH_4]_2SO_4$). The dialysate is subsequently concentrated with the help of concentration filters (Amicon Ultra-30, Merk Millipore). Concentrated enzyme is distributed in small aliquots, 50% glycerol final is added, and those aliquots are then frozen at −20° C. and stored for long term. 5 µL of various fraction of the purified enzymes are analyzed in SDS-PAGE gels.

Example 2: Efficiency of TdT Variants for Synthesizing Difficult Sequences

As noted above, the invention is based in part on a recognition and appreciation by the inventors that certain nucleotide sequences are difficult for TdTs to extend. Thus, an object of this experiment was to discover new TdT variants that exhibit enhanced capability to synthesize such difficult sequences based on comparison to an earlier TdT variant, designated M27 (SEQ ID NO: 32). In this example, a mutation library of mouse TdT (SEQ ID NO: 3) was produced based on structural information from mouse TdT, the activities of TdT variants from prior libraries, and from conventional protein engineering techniques. TdT variants from the library are expressed and purified as described above and were screened for their capability to synthesize certain difficult-to-synthesize sequences (shown in Table 7) at a higher rate than that of M27. Synthesis of the short sequences was performed by repeating 5 cycles of synthesis wherein each cycle comprises two steps: (i) an extension step (typical reaction volume 200 µL) wherein a primer (or initiator) is incubated for 3 min at 37° C. with 1 mM of a 3'-O—NH2-dXTP and a defined concentration of TdT variant in the activity buffer (X can be A, T, C or G depending on the sequence to synthesized; for example, to synthesize AACTA, X=A for the first cycle, X=A for the second cycle, X=C for the third cycle, and so on); and (ii) a deprotection step (typical reaction volume 200 μL) to deblock the extended primer to remove the 3'-protection group and allow a second extension step. The deblocking reaction is performed in 700 mM NaNO$_2$, 1 M Sodium Acetate, pH=5.5 for 3 min. Volume of reaction is typically 200 μL (e.g. see Benner, U.S. Pat. No. 7,544,794). The extended primer is linked to a solid support that allows removal of the reaction buffer between each step. As noted above, the reactions were run for 3 min at 37° C. after which the extended primers were (i) cleaved from their supports, (ii) separated by electrophoresis and (iii) the fluorescent intensity of the bands was measured to evaluate the efficiency of synthesis for each variant. The results are shown in Table 7 where the entries are relative values that reflect the relative extension rates among the variants.

TABLE 7

Synthesis Efficiency of Various TdT Variants

| Variant | 3' Sequences of Test Initiators | | | | |
|---|---|---|---|---|---|
| | -AACTA | -AAGCT | -CCCCA | -GGCAT | -GGCTG |
| DS1017 (M27) SEQ ID NO: 32 | 75 | 96 | 26 | 96 | 56 |
| Lib34-20 | 72 | 96 | 18 | 96 | 57 |
| DS1002 (M44-1) | 74 | 97 | 50 | 97 | 36 |
| DS1002 (M44-2) | 78 | 95 | 50 | 96 | 35 |

TABLE 7-continued

Synthesis Efficiency of Various TdT Variants

| Variant | 3' Sequences of Test Initiators | | | | |
|---|---|---|---|---|---|
| | -AACTA | -AAGCT | -CCCCA | -GGCAT | -GGCTG |
| DS1004 (M45) | 84 | 97 | 59 | 95 | 58 |
| DS1006 (M46) | 93 | 96 | 28 | 96 | 71 |
| DS1007 (M47) | 92 | 97 | 30 | 96 | 78 |
| Lib34-16 | 91 | 94 | 7 | 0 | 75 |

An inspection of the sequences of the variants that exceed extension activity of M27 for one or more of the test initiators showed that each one at least possessed a substitution at Q326 and usually shared one or more additional substitutions from the set K265, H337, W377, A17 and G57, with respect to SEQ ID NO: 3.

Elongation efficiency of variants M27, M44 and M45 were also measured under different reaction temperatures. In these experiments only a single elongation step was performed. The Reaction conditions were as follows: primer (i.e. initiator) concentration of 0.5 μM, a single 3'-ONH2-dTTP at 125 μM, and TdT reaction buffer (for example, available from New England Biolabs) supplemented with CoCl$_2$. Separate reactions were run using different primers (not attached to supports) having different compositions and lengths in the range of from 20 to 25 nucleotides. Primers were labeled with an ATTO fluorescent dye on the 5' extremity. The reactions were run for 10 min separately at 37° C., 45° C., 50° C. and 55° C. The results are shown in Table 8 where the values in the Table are relative magnitudes.

TABLE 8

Optimal Extension Reaction Temperatures For Various TdT Variants

| | Incorporation on Mixed Nucleotide Primer | | | | Incorporation on PolyC Primer | | | |
|---|---|---|---|---|---|---|---|---|
| | Temperature | | | | | | | |
| | 37° C. | 45° C. | 50° C. | 55° C. | 37° C. | 45° C. | 50° C. | 55° C. |
| DS1017 (M27) SEQ ID NO: 32 | 63 | 100 | 77 | 24 | 71 | 97 | 100 | 44 |
| DS1002 (M44) | 95 | 131 | 137 | 120 | 78 | 104 | 127 | 128 |
| DS1004 (M45) | 62 | 101 | 105 | 82 | 72 | 101 | 122 | 116 |

The data show that M44 and M45 exhibit equivalently higher yields than M27 at temperatures of 50° C. and above, which is evidence of greater temperature stability.

Example 3: TdT Variants of Various Species

In this example, non-mouse TdT variants were constructed from publicly available genes and were tested to determine their ability to incorporate 3'-O-amino-dNTPs into a test polynucleotide (p877) in hairpin completion assays as described above. The TdT variants are identified in Table 9 along with their incorporation capacity as compared to mouse TdT variant, M27.

TABLE 9

Characteristics of Non-Mouse TdT Variants

| Species | Accession Number Of sources species | Percent Identity to M27 | Percent Activity Relative to M27* | SEQ ID NO |
|---|---|---|---|---|
| Bovine | NP_803461.1 | 82 | 484 | 27 |
| Related to Latmeria | XP_005999893.1 | 80 | 31 | 28 |
| Puma | XP_026918530.1 | 81 | 54 | 29 |
| N139 reptilian | XP_016851390.1 | 68 | 131 | 30 |
| Shrew | XP_006880141.1 | 82 | 57 | 31 |
| Mouse M27 | | 100 | — | 32 |

*Hairpin completion assay

Definitions

Amino acids are represented by either their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

"Functionally equivalent" in reference to a substituted residue means the substituted residue of a variant TdT has an identical functional role as a residue in a sequence of another TdT having a sequence homologous to SEQ ID NO: 1. Functionally equivalent residues may be identified by using sequence alignments, for example, using the Mutalin line alignment software (http://multalin.toulouse.inra.fr/multalin/multalin.html; 1988, Nucl. Acids Res., 16 (22), 25 10881-10890). After alignment, the functionally equivalent residues are at homologous positions on the different sequences considered. Sequence alignments and identification of functionally equivalent residues may be determined between any TdT and their natural variants, including interspecies.

"Isolated" in reference to protein means such a compound which has been identified and separated and/or recovered from a component of its natural environment or from a heterogeneous reaction mixture. Contaminant components of a natural environment or reaction mixture are materials which would interfere with a protein's function, and may include enzymes, hormones, and other proteinaceous or nonproteinaceous solutes. In some embodiments, a protein of the invention is purified (1) to greater than 95% by weight of protein as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. When manufactured by recombinant methodologies, an isolated protein of the invention may include the protein of the invention in situ within recombinant cells since at least one component of the protein's natural environment will not be present. Ordinarily, an isolated protein of the invention is prepared by at least one purification step.

"Kit" refers to any delivery system for delivering materials or reagents for carrying out a method of the invention. In the context of reaction assays, such delivery systems include systems and/or compounds (such as dilutants, surfactants, carriers, or the like) that allow for the storage, transport, or delivery of reaction reagents (e.g., one or more TdT variants, reaction buffers, 3'-O-protected-dNTPs, deprotection reagents, solid supports with initiators attached, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain one or more TdT variants for use in a synthesis method, while a second or additional containers may contain deprotection agents, solid supports with initiators, 3'-O-protected dNTPs, or the like.

"Mutant" or "variant," which are used interchangeably, refer to polypeptides derived from a natural or reference TdT polypeptide described herein, and comprising a modification or an alteration, i.e., a substitution, insertion, and/or deletion, at one or more positions. Variants may be obtained by various techniques well known in the art. In particular, examples of techniques for altering the DNA sequence encoding the wild-type protein, include, but are not limited to, site-directed mutagenesis, random mutagenesis, sequence shuffling and synthetic oligonucleotide construction. Mutagenesis activities consist in deleting, inserting or substituting one or several amino-acids in the sequence of a protein or in the case of the invention of a polymerase. The following terminology is used to designate a substitution: L238A denotes that amino acid residue (Leucine, L) at position 238 of a reference, or wild type, sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

"Sequence identity" refers to the number (or fraction, usually expressed as a percentage) of matches (e.g., identical amino acid residues) between two sequences, such as two polypeptide sequences or two polynucleotide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithm (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as http://blast.ncbi.nlm.nih.gov/or ttp://www.ebi.ac.uk/Tools/emboss/. Those skilled in the art can determine appropriate parameters for measuring alignment, including any algorithm needed to achieve maximal alignment over the full length of the sequences being compared. For purposes herein, % amino acid sequence identity values refer to values generated using the pair wise sequence alignment program EMBOSS Needle, that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

"Polynucleotide" or "oligonucleotide" are used interchangeably and each mean a linear polymer of nucleotide monomers or analogs thereof. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2nd Edition (Cold Spring Harbor Press, New York, 2003).

A "substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues. The sign "+" indicates a combination of substitutions.

The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

In the present document, the following terminology is used to designate a substitution: L238A denotes that amino acid residue (Leucine, L) at position 238 of the parent sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

The invention claimed is:

1. A terminal deoxynucleotidyl transferase (TdT) variant comprising an amino acid sequence at least ninety percent identical to the amino acid sequence of SEQ ID NO: 3 with a substitution at positions Q326 and K265, wherein the TdT variant (i) is capable of synthesizing a nucleic acid fragment without a template and (ii) is capable of incorporating a 3'-O-modified nucleotide onto a nucleic acid fragment.

2. The TdT variant of claim 1 further comprising one or more of:
   (i) a substitution at position H337 with respect to SEQ ID NO 3;
   (ii) a substitution at position W377 with respect to SEQ ID NO 3;
   (iii) a substitution at position A17 with respect to SEQ ID NO 3;
   (iv) a substitution at position G57 with respect to SEQ ID NO 3; or
   (v) a substitution at position Q261 with respect to SEQ ID NO: 3.

3. The TdT variant of claim 1 wherein:
   (i) said substitution at position Q326 with respect to SEQ ID NO 3 is selected from the group consisting of T, F, L, M, I, V and Y;
   (ii) said substitution at position K265 with respect to SEQ ID NO 3 is selected from the group consisting of E, T, A and R.

4. The TdT variant of claim 1 further comprising one or more of:
   (i) a substitution at position L52 with respect to SEQ ID NO: 3;
   (ii) a substitution at position M63 with respect to SEQ ID NO: 3;
   (iii) a substitution at position A108 with respect to SEQ ID NO: 3;
   (iv) a substitution at position L131 with respect to SEQ ID NO: 3;
   (v) a substitution at position C173 with respect to SEQ ID NO: 3;
   (vi) a substitution at position R207 with respect to SEQ ID NO: 3;
   (vii) a substitution at position G284 with respect to SEQ ID NO: 3;
   (viii) a substitution at position E289 with respect to SEQ ID NO: 3;
   (ix) a substitution at position R325 with respect to SEQ ID NO: 3;
   (x) a substitution at position E328 with respect to SEQ ID NO: 3; or
   (xi) a substitution at position R351 with respect to SEQ ID NO: 3.

5. The TdT variant of claim 1 further comprising one or more of:
   (i) a substitution Q37E with respect to SEQ ID NO: 3;
   (ii) a substitution D41R with respect to SEQ ID NO: 3;
   (iii) a substitution C59R with respect to SEQ ID NO: 3;
   (iv) a substitution L60D with respect to SEQ ID NO: 3;
   (v) a substitution S94R with respect to SEQ ID NO: 3;
   (vi) a substitution G98E with respect to SEQ ID NO: 3;
   (vii) a substitution S119A with respect to SEQ ID NO: 3;
   (viii) a substitution S146E with respect to SEQ ID NO: 3;
   (ix) a substitution Q149R with respect to SEQ ID NO: 3;
   (x) a substitution F193Y with respect to SEQ ID NO: 3;
   (xi) a substitution V199M with respect to SEQ ID NO: 3; or
   (xii) a substitution M201V with respect to SEQ ID NO: 3.

6. The TdT variant of claim 1 comprising the following combination of substitutions with respect to SEQ ID NO: 3:
   (i) A17V+Q37E+D41R+L52F+G57E+M63R+S94R+G98E+A108V+S119A+L131R+S146E+Q149R+C173G+R207L+K265T+G284P+E289V+R325P+Q326F+E328N+H337D+R351K+W377R;
   (ii) A17V+Q37E+D41R+L52F+G57E+M63R+S94R+G98E+A108V+S146E+Q149R+C173G+F193Y+V199M+M201V+R207L+K265T+G284P+E289V+R325A+Q326F+E328N+R351K;
   (iii) L52F+A108V+R351K+A17V+Q37E+D41R+G57E+C59R+L60D+M63R+S94R+G98E+S119A+L131R+S146E+Q149R+C173G+R207L+K265T+G284P+E289V+R325A+Q326F+E328N;
   (iv) L52F+A108V+R351K+A17V+Q37E+D41R+G57E+C59R+L60D+M63R+S94R+G98E+K118Q+S119A+L131R+S146E+Q149R+C173G+R207L+K265T+G284P+E289V+R325A+Q326F+E328N+W377R;
   (v) A17V+Q37E+D41R+L52F+G57E+C59R+L60D+M63R+S94R+G98E+A108V+S119A+L131R+S146E+Q149R+C173G+R207L+F259S+Q261L, G284P+E289V+R325A+Q326F+E328N+R351K+W377R;
   (vi) A17V+Q37E+D41R+L52F+G57E+C59R+L60D+M63R+S94R+G98E+A108V+S119A+L131R+S146E+Q149R+C173G+R207L+E257D+F259S+K260R+Q261L+G284P+E289V+R325A+Q326F+E328N+R351K+W377R;
   (vii) A17V+D41R+L53F+G57E+C59R+L60D+M63R+S94R+G98E+K118Q+S119A+L131R+S146E+Q149R+C173G+R207L+K265T+G284P+E289V+R325A+Q326F+R351K+W377R;

(viii) A17V+D41R+L52F+G57E+C59R+L60D+M63R+ S94R+G98E+A108V+S119A+L131R+S146E+ Q149R+R207L+K265T+G284P+E289V+R325A+ Q326F+R351K;
(ix) A17V+L52F+M63R+A108V+C173G+R207L+ K265T+G284P+E289V+R325P+E328N+R351K;
(x) A17V+D41R+L52F+G57E+M63R+S94R+G98E+ A108V+S146E+Q149R+C173G+M184T+R207L+ K209H+G284L+E289A+R325V+E328K+R351K;
(xi) A17V+L52F+G57E+M63R+A108V+C173G+ R207L+K265T+G284P+E289V+R325P+E328N+ R351K; or
(xii) A17V+L32T+Q37R+D41R+L52F+G57E+C59R+ L60D+M63R+S67A+S94R+G98E+A108V+S119A+ L131R+S146E+Q149R+V171A+S172E+C173R+ V182I+S183E+R207L+K209H+M210K+T211I+ E223G+A224P+E228D+Q261L+G284P+E289V+ R325A+Q326F+E328N+R351K+D372E.

7. A method of synthesizing a polynucleotide having a predetermined sequence, the method comprising the steps of:
   a) providing an initiator having a 3'-terminal nucleotide having a free 3'-hydroxyl;
   b) repeating cycles of (i) contacting under elongation conditions the initiator or elongated fragments having free 3'-O-hydroxyls with a 3'-O-blocked nucleoside triphosphate and a TdT variant according to claim 1, so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, until the polynucleotide is formed.

8. The method of claim 7, wherein said 3'-O-blocked nucleoside triphosphate is a 3'-O-NH2-nucleoside triphosphate, a 3'-O-azidomethyl-nucleoside triphosphate, a 3'-O-allyl-nucleoside triphosphate, or a 3'-O-(2-nitrobenzyl)-nucleoside triphosphate.

9. A kit for performing a nucleotide incorporation reaction comprising:
   a) a variant of TdT according to claim 1,
   b) one or more nucleotides, preferably one or more 3'O-modified nucleotides, and
   c) optionally at least one nucleic acid primer.

10. The TdT variant of claim 2, wherein:
   (i) said substitution of at position H337 with respect to SEQ ID NO: 3 is selected from the group consisting of Y, F, N and D;
   (ii) said substitution at position W377 with respect to SEQ ID NO: 3 is R;
   (iii) said substitution at position A17 with respect to SEQ ID NO: 3 is V, I or L;
   (iv) said substitution at position G57 with respect to SEQ ID NO: 3 is E; and
   (v) said substitution at position Q261 with respect to SEQ ID NO: 3 is R.

* * * * *

SEQUENCE LISTING

```
<160> NUMBER OF SEQ ID NOS: 34

<210> SEQ ID NO 1
<211> LENGTH: 510
<212> TYPE: PRT
<213> ORGANISM: ARTIFICIAL SEQUENCE
<220> FEATURE:
```

<223> OTHER INFORMATION: TdT PROTEIN

<400> SEQUENCE: 1

```
Met Asp Pro Leu Gln Ala Val His Leu Gly Pro Arg Lys Lys Arg Pro
 1               5                  10                  15

Arg Gln Leu Gly Thr Pro Val Ala Ser Thr Pro Tyr Asp Ile Arg Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
 65                  70                  75                  80

Gly Ser Asp Val Leu Glu Trp Leu Gln Leu Gln Asn Ile Lys Ala Ser
                85                  90                  95

Ser Glu Leu Glu Leu Leu Asp Ile Ser Trp Leu Ile Glu Cys Met Gly
            100                 105                 110

Ala Gly Lys Pro Val Glu Met Met Gly Arg His Gln Leu Val Val Asn
        115                 120                 125

Arg Asn Ser Ser Pro Ser Pro Val Pro Gly Ser Gln Asn Val Pro Ala
    130                 135                 140

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
                165                 170                 175

Glu Asn Asp Glu Leu Arg Glu Asn Glu Gly Ser Cys Leu Ala Phe Met
            180                 185                 190

Arg Ala Ser Ser Val Leu Lys Ser Leu Pro Phe Pro Ile Thr Ser Met
        195                 200                 205

Lys Asp Thr Glu Gly Ile Pro Cys Leu Gly Asp Lys Val Lys Ser Ile
    210                 215                 220

Ile Glu Gly Ile Ile Glu Asp Gly Glu Ser Ser Glu Ala Lys Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ala Glu Lys Trp Phe Arg Met Gly Phe Arg
            260                 265                 270

Thr Leu Ser Lys Ile Gln Ser Asp Lys Ser Leu Arg Phe Thr Gln Met
        275                 280                 285

Gln Lys Ala Gly Phe Leu Tyr Tyr Glu Asp Leu Val Ser Cys Val Asn
    290                 295                 300

Arg Pro Glu Ala Glu Ala Val Ser Met Leu Val Lys Glu Ala Val Val
305                 310                 315                 320

Thr Phe Leu Pro Asp Ala Leu Val Thr Met Thr Gly Gly Phe Arg Arg
                325                 330                 335

Gly Lys Met Thr Gly His Asp Val Asp Phe Leu Ile Thr Ser Pro Glu
            340                 345                 350

Ala Thr Glu Asp Glu Glu Gln Gln Leu Leu His Lys Val Thr Asp Phe
        355                 360                 365

Trp Lys Gln Gln Gly Leu Leu Leu Tyr Cys Asp Ile Leu Glu Ser Thr
    370                 375                 380

Phe Glu Lys Phe Lys Gln Pro Ser Arg Lys Val Asp Ala Leu Asp His
385                 390                 395                 400
```

```
Phe Gln Lys Cys Phe Leu Ile Leu Lys Leu Asp His Gly Arg Val His
                405                 410                 415
Ser Glu Lys Ser Gly Gln Gln Glu Gly Lys Gly Trp Lys Ala Ile Arg
            420                 425                 430
Val Asp Leu Val Met Cys Pro Tyr Asp Arg Arg Ala Phe Ala Leu Leu
        435                 440                 445
Gly Trp Thr Gly Ser Arg Gln Phe Glu Arg Asp Leu Arg Arg Tyr Ala
    450                 455                 460
Thr His Glu Arg Lys Met Met Leu Asp Asn His Ala Leu Tyr Asp Arg
465                 470                 475                 480
Thr Lys Arg Val Phe Leu Glu Ala Glu Ser Glu Glu Ile Phe Ala
                485                 490                 495
His Leu Gly Leu Asp Tyr Ile Glu Pro Trp Glu Arg Asn Ala
            500                 505                 510

<210> SEQ ID NO 2
<211> LENGTH: 18
<212> TYPE: DNA
<213> ORGANISM: ARTIFICIAL SEQUENCE
<220> FEATURE:
<223> OTHER INFORMATION: PRIMER

<400> SEQUENCE: 2
aaaaaaaaaa aaaagggg                                               18

<210> SEQ ID NO 3
<211> LENGTH: 381
<212> TYPE: PRT
<213> ORGANISM: ARTIFICIAL SEQUENCE
<220> FEATURE:
<223> OTHER INFORMATION: truncated mouse sequence

<400> SEQUENCE: 3

Asn Ser Ser Pro Ser Pro Val Pro Gly Ser Gln Asn Val Pro Ala Pro
1               5                   10                  15
Ala Val Lys Lys Ile Ser Gln Tyr Ala Cys Gln Arg Arg Thr Thr Leu
            20                  25                  30
Asn Asn Tyr Asn Gln Leu Phe Thr Asp Ala Leu Asp Ile Leu Ala Glu
        35                  40                  45
Asn Asp Glu Leu Arg Glu Asn Glu Gly Ser Cys Leu Ala Phe Met Arg
    50                  55                  60
Ala Ser Ser Val Leu Lys Ser Leu Pro Phe Pro Ile Thr Ser Met Lys
65                  70                  75                  80
Asp Thr Glu Gly Ile Pro Cys Leu Gly Asp Lys Val Lys Ser Ile Ile
                85                  90                  95
Glu Gly Ile Ile Glu Asp Gly Glu Ser Ser Glu Ala Lys Ala Val Leu
            100                 105                 110
Asn Asp Glu Arg Tyr Lys Ser Phe Lys Leu Phe Thr Ser Val Phe Gly
        115                 120                 125
Val Gly Leu Lys Thr Ala Glu Lys Trp Phe Arg Met Gly Phe Arg Thr
    130                 135                 140
Leu Ser Lys Ile Gln Ser Asp Lys Ser Leu Arg Phe Thr Gln Met Gln
145                 150                 155                 160
Lys Ala Gly Phe Leu Tyr Tyr Glu Asp Leu Val Ser Cys Val Asn Arg
                165                 170                 175
Pro Glu Ala Glu Ala Val Ser Met Leu Val Lys Glu Ala Val Val Thr
            180                 185                 190
```

Phe Leu Pro Asp Ala Leu Val Thr Met Thr Gly Gly Phe Arg Arg Gly
            195                 200                 205

Lys Met Thr Gly His Asp Val Asp Phe Leu Ile Thr Ser Pro Glu Ala
        210                 215                 220

Thr Glu Asp Glu Glu Gln Gln Leu Leu His Lys Val Thr Asp Phe Trp
225                 230                 235                 240

Lys Gln Gln Gly Leu Leu Tyr Cys Asp Ile Leu Glu Ser Thr Phe
                245                 250                 255

Glu Lys Phe Lys Gln Pro Ser Arg Lys Val Asp Ala Leu Asp His Phe
                260                 265                 270

Gln Lys Cys Phe Leu Ile Leu Lys Leu Asp His Gly Arg Val His Ser
            275                 280                 285

Glu Lys Ser Gly Gln Gln Glu Gly Lys Gly Trp Lys Ala Ile Arg Val
        290                 295                 300

Asp Leu Val Met Cys Pro Tyr Asp Arg Arg Ala Phe Ala Leu Leu Gly
305                 310                 315                 320

Trp Thr Gly Ser Arg Gln Phe Glu Arg Asp Leu Arg Tyr Ala Thr
                325                 330                 335

His Glu Arg Lys Met Met Leu Asp Asn His Ala Leu Tyr Asp Arg Thr
                340                 345                 350

Lys Arg Val Phe Leu Glu Ala Glu Ser Glu Glu Ile Phe Ala His
            355                 360                 365

Leu Gly Leu Asp Tyr Ile Glu Pro Trp Glu Arg Asn Ala
            370                 375                 380

<210> SEQ ID NO 4
<211> LENGTH: 380
<212> TYPE: PRT
<213> ORGANISM: ARTIFICIAL SEQUENCE
<220> FEATURE:
<223> OTHER INFORMATION: Bovine truncated catalytic domain

<400> SEQUENCE: 4

Asp Tyr Ser Ala Thr Pro Asn Pro Gly Phe Gln Lys Thr Pro Pro Leu
1               5                   10                  15

Ala Val Lys Lys Ile Ser Gln Tyr Ala Cys Gln Arg Lys Thr Thr Leu
            20                  25                  30

Asn Asn Tyr Asn His Ile Phe Thr Asp Ala Phe Glu Ile Leu Ala Glu
        35                  40                  45

Asn Ser Glu Phe Lys Glu Asn Glu Val Ser Tyr Val Thr Phe Met Arg
    50                  55                  60

Ala Ala Ser Val Leu Lys Ser Leu Pro Phe Thr Ile Ile Ser Met Lys
65                  70                  75                  80

Asp Thr Glu Gly Ile Pro Cys Leu Gly Asp Lys Val Lys Cys Ile Ile
                85                  90                  95

Glu Glu Ile Ile Glu Asp Gly Glu Ser Ser Glu Val Lys Ala Val Leu
            100                 105                 110

Asn Asp Glu Arg Tyr Gln Ser Phe Lys Leu Phe Thr Ser Val Phe Gly
        115                 120                 125

Val Gly Leu Lys Thr Ser Glu Lys Trp Phe Arg Met Gly Phe Arg Ser
    130                 135                 140

Leu Ser Lys Ile Met Ser Asp Lys Thr Leu Lys Phe Thr Lys Met Gln
145                 150                 155                 160

Lys Ala Gly Phe Leu Tyr Tyr Glu Asp Leu Val Ser Cys Val Thr Arg
                165                 170                 175

```
Ala Glu Ala Glu Ala Val Gly Val Leu Val Lys Glu Ala Val Trp Ala
            180                 185                 190

Phe Leu Pro Asp Ala Phe Val Thr Met Thr Gly Gly Phe Arg Arg Gly
        195                 200                 205

Lys Lys Ile Gly His Asp Val Asp Phe Leu Ile Thr Ser Pro Gly Ser
        210                 215                 220

Ala Glu Asp Glu Glu Gln Leu Leu Pro Lys Val Ile Asn Leu Trp Glu
225                 230                 235                 240

Lys Lys Gly Leu Leu Leu Tyr Tyr Asp Leu Val Glu Ser Thr Phe Glu
            245                 250                 255

Lys Phe Lys Leu Pro Ser Arg Gln Val Asp Thr Leu Asp His Phe Gln
        260                 265                 270

Lys Cys Phe Leu Ile Leu Lys Leu His His Gln Arg Val Asp Ser Ser
        275                 280                 285

Lys Ser Asn Gln Gln Glu Gly Lys Thr Trp Lys Ala Ile Arg Val Asp
        290                 295                 300

Leu Val Met Cys Pro Tyr Glu Asn Arg Ala Phe Ala Leu Leu Gly Trp
305                 310                 315                 320

Thr Gly Ser Arg Gln Phe Glu Arg Asp Ile Arg Arg Tyr Ala Thr His
            325                 330                 335

Glu Arg Lys Met Met Leu Asp Asn His Ala Leu Tyr Asp Lys Thr Lys
            340                 345                 350

Arg Val Phe Leu Lys Ala Glu Ser Glu Glu Ile Phe Ala His Leu
        355                 360                 365

Gly Leu Asp Tyr Ile Glu Pro Trp Glu Arg Asn Ala
    370                 375                 380

<210> SEQ ID NO 5
<211> LENGTH: 380
<212> TYPE: PRT
<213> ORGANISM: ARTIFICIAL SEQUENCE
<220> FEATURE:
<223> OTHER INFORMATION: Human truncated

<400> SEQUENCE: 5

Asp Tyr Ser Asp Ser Thr Asn Pro Gly Pro Lys Thr Pro Pro Ile
1               5                   10                  15

Ala Val Gln Lys Ile Ser Gln Tyr Ala Cys Gln Arg Arg Thr Thr Leu
            20                  25                  30

Asn Asn Cys Asn Gln Ile Phe Thr Asp Ala Phe Asp Ile Leu Ala Glu
        35                  40                  45

Asn Cys Glu Phe Arg Glu Asn Glu Asp Ser Cys Val Thr Phe Met Arg
    50                  55                  60

Ala Ala Ser Val Leu Lys Ser Leu Pro Phe Thr Ile Ile Ser Met Lys
65                  70                  75                  80

Asp Thr Glu Gly Ile Pro Cys Leu Gly Ser Lys Val Lys Gly Ile Ile
            85                  90                  95

Glu Glu Ile Ile Glu Asp Gly Glu Ser Ser Glu Val Lys Ala Val Leu
            100                 105                 110

Asn Asp Glu Arg Tyr Gln Ser Phe Lys Leu Phe Thr Ser Val Phe Gly
        115                 120                 125

Val Gly Leu Lys Thr Ser Glu Lys Trp Phe Arg Met Gly Phe Arg Thr
    130                 135                 140

Leu Ser Lys Val Arg Ser Asp Lys Ser Leu Lys Phe Thr Arg Met Gln
145                 150                 155                 160
```

-continued

```
Lys Ala Gly Phe Leu Tyr Tyr Glu Asp Leu Val Ser Cys Val Thr Arg
            165                 170                 175

Ala Glu Ala Glu Ala Val Ser Val Leu Val Lys Glu Ala Val Trp Ala
        180                 185                 190

Phe Leu Pro Asp Ala Phe Val Thr Met Thr Gly Gly Phe Arg Arg Gly
        195                 200                 205

Lys Lys Met Gly His Asp Val Asp Phe Leu Ile Thr Ser Pro Gly Ser
        210                 215                 220

Thr Glu Asp Glu Glu Gln Leu Leu Gln Lys Val Met Asn Leu Trp Glu
225                 230                 235                 240

Lys Lys Gly Leu Leu Leu Tyr Tyr Asp Leu Val Glu Ser Thr Phe Glu
                245                 250                 255

Lys Leu Arg Leu Pro Ser Arg Lys Val Asp Ala Leu Asp His Phe Gln
            260                 265                 270

Lys Cys Phe Leu Ile Phe Lys Leu Pro Arg Gln Arg Val Asp Ser Asp
            275                 280                 285

Gln Ser Ser Trp Gln Glu Gly Lys Thr Trp Lys Ala Ile Arg Val Asp
        290                 295                 300

Leu Val Leu Cys Pro Tyr Glu Arg Arg Ala Phe Ala Leu Leu Gly Trp
305                 310                 315                 320

Thr Gly Ser Arg Gln Phe Glu Arg Asp Leu Arg Arg Tyr Ala Thr His
                325                 330                 335

Glu Arg Lys Met Ile Leu Asp Asn His Ala Leu Tyr Asp Lys Thr Lys
            340                 345                 350

Arg Ile Phe Leu Lys Ala Glu Ser Glu Glu Ile Phe Ala His Leu
            355                 360                 365

Gly Leu Asp Tyr Ile Glu Pro Trp Glu Arg Asn Ala
        370                 375                 380
```

<210> SEQ ID NO 6
<211> LENGTH: 376
<212> TYPE: PRT
<213> ORGANISM: ARTIFICIAL SEQUENCE
<220> FEATURE:
<223> OTHER INFORMATION: Chicken 1 truncated

<400> SEQUENCE: 6

```
Gln Tyr Pro Thr Leu Lys Thr Pro Glu Ser Glu Val Ser Ser Phe Thr
1               5                   10                  15

Ala Ser Lys Val Ser Gln Tyr Ser Cys Gln Arg Lys Thr Thr Leu Asn
            20                  25                  30

Asn Cys Asn Lys Lys Phe Thr Asp Ala Phe Glu Ile Met Ala Glu Asn
        35                  40                  45

Tyr Glu Phe Lys Glu Asn Glu Ile Phe Cys Leu Glu Phe Leu Arg Ala
    50                  55                  60

Ala Ser Val Leu Lys Ser Leu Pro Phe Pro Val Thr Arg Met Lys Asp
65                  70                  75                  80

Ile Gln Gly Leu Pro Cys Met Gly Asp Arg Val Arg Asp Val Ile Glu
                85                  90                  95

Glu Ile Ile Glu Glu Gly Glu Ser Ser Arg Ala Lys Asp Val Leu Asn
            100                 105                 110

Asp Glu Arg Tyr Lys Ser Phe Lys Glu Phe Thr Ser Val Phe Gly Val
        115                 120                 125

Gly Val Lys Thr Ser Glu Lys Trp Phe Arg Met Gly Leu Arg Thr Val
    130                 135                 140
```

```
Glu Glu Val Lys Ala Asp Lys Thr Leu Lys Leu Ser Lys Met Gln Arg
145                 150                 155                 160

Ala Gly Phe Leu Tyr Tyr Glu Asp Leu Val Ser Cys Val Ser Lys Ala
            165                 170                 175

Glu Ala Asp Ala Val Ser Ser Ile Val Lys Asn Thr Val Cys Thr Phe
        180                 185                 190

Leu Pro Asp Ala Leu Val Thr Ile Thr Gly Gly Phe Arg Arg Gly Lys
    195                 200                 205

Lys Ile Gly His Asp Ile Asp Phe Leu Ile Thr Ser Pro Gly Gln Arg
210                 215                 220

Glu Asp Asp Glu Leu Leu His Lys Gly Leu Leu Leu Tyr Cys Asp Ile
225                 230                 235                 240

Ile Glu Ser Thr Phe Val Lys Glu Gln Ile Pro Ser Arg His Val Asp
            245                 250                 255

Ala Met Asp His Phe Gln Lys Cys Phe Ala Ile Leu Lys Leu Tyr Gln
        260                 265                 270

Pro Arg Val Asp Asn Ser Ser Tyr Asn Met Ser Lys Lys Cys Asp Met
    275                 280                 285

Ala Glu Val Lys Asp Trp Lys Ala Ile Arg Val Asp Leu Val Ile Thr
290                 295                 300

Pro Phe Glu Gln Tyr Ala Tyr Ala Leu Leu Gly Trp Thr Gly Ser Arg
305                 310                 315                 320

Gln Phe Gly Arg Asp Leu Arg Arg Tyr Ala Thr His Glu Arg Lys Met
            325                 330                 335

Met Leu Asp Asn His Ala Leu Tyr Asp Lys Arg Lys Arg Val Phe Leu
        340                 345                 350

Lys Ala Gly Ser Glu Glu Glu Ile Phe Ala His Leu Gly Leu Asp Tyr
    355                 360                 365

Val Glu Pro Trp Glu Arg Asn Ala
370                 375

<210> SEQ ID NO 7
<211> LENGTH: 387
<212> TYPE: PRT
<213> ORGANISM: ARTIFICIAL SEQUENCE
<220> FEATURE:
<223> OTHER INFORMATION: Possum truncated

<400> SEQUENCE: 7

Ser Ala Asn Pro Asp Pro Thr Ala Gly Thr Leu Asn Ile Leu Pro Pro
1               5                   10                  15

Thr Thr Lys Thr Ile Ser Gln Tyr Ala Cys Gln Arg Arg Thr Thr Ile
            20                  25                  30

Asn Asn His Asn Gln Arg Phe Thr Asp Ala Phe Glu Ile Leu Ala Lys
        35                  40                  45

Asn Tyr Glu Phe Lys Glu Asn Asp Asp Thr Cys Leu Thr Phe Met Arg
    50                  55                  60

Ala Ile Ser Val Leu Lys Cys Leu Pro Phe Glu Val Val Ser Leu Lys
65                  70                  75                  80

Asp Thr Glu Gly Leu Pro Trp Ile Gly Asp Glu Val Lys Gly Ile Met
            85                  90                  95

Glu Glu Ile Ile Glu Asp Gly Glu Ser Leu Glu Val Gln Ala Val Leu
        100                 105                 110

Asn Asp Glu Arg Tyr Gln Ser Phe Lys Leu Phe Thr Ser Val Phe Gly
    115                 120                 125
```

Val Gly Leu Lys Thr Ala Asp Lys Trp Tyr Arg Met Gly Phe Arg Thr
130                 135                 140

Leu Asn Lys Ile Arg Ser Asp Lys Thr Leu Lys Leu Thr Lys Met Gln
145                 150                 155                 160

Lys Ala Gly Leu Cys Tyr Tyr Glu Asp Leu Ile Asp Cys Val Ser Lys
                165                 170                 175

Ala Glu Ala Asp Ala Val Ser Leu Leu Val Gln Asp Ala Val Trp Thr
            180                 185                 190

Phe Leu Pro Asp Ala Leu Val Thr Ile Thr Gly Gly Phe Arg Arg Gly
        195                 200                 205

Lys Glu Phe Gly His Asp Val Asp Phe Leu Ile Thr Ser Pro Gly Ala
210                 215                 220

Glu Lys Glu Gln Glu Asp Gln Leu Leu Gln Lys Val Thr Asn Leu Trp
225                 230                 235                 240

Lys Lys Gln Gly Leu Leu Leu Tyr Cys Asp Leu Ile Glu Ser Thr Phe
                245                 250                 255

Glu Asp Leu Lys Leu Pro Ser Arg Lys Ile Asp Ala Leu Asp His Phe
            260                 265                 270

Gln Lys Cys Phe Leu Ile Leu Lys Leu Tyr His His Lys Glu Asp Lys
        275                 280                 285

Arg Lys Trp Glu Met Pro Thr Gly Ser Asn Glu Ser Glu Ala Lys Ser
290                 295                 300

Trp Lys Ala Ile Arg Val Asp Leu Val Val Cys Pro Tyr Asp Arg Tyr
305                 310                 315                 320

Ala Phe Ala Leu Leu Gly Trp Ser Gly Ser Arg Gln Phe Glu Arg Asp
                325                 330                 335

Leu Arg Arg Tyr Ala Thr His Glu Lys Lys Met Met Leu Asp Asn His
            340                 345                 350

Ala Leu Tyr Asp Lys Thr Lys Lys Ile Phe Leu Lys Ala Lys Ser Glu
        355                 360                 365

Glu Glu Ile Phe Ala His Leu Gly Leu Glu Tyr Ile Gln Pro Ser Glu
370                 375                 380

Arg Asn Ala
385

<210> SEQ ID NO 8
<211> LENGTH: 381
<212> TYPE: PRT
<213> ORGANISM: ARTIFICIAL SEQUENCE
<220> FEATURE:
<223> OTHER INFORMATION: New truncated shrew

<400> SEQUENCE: 8

Asp Cys Pro Ala Ser His Asp Ser Ser Pro Gln Lys Thr Glu Ser Ala
1               5                   10                  15

Ala Val Gln Lys Ile Ser Gln Tyr Ala Cys Gln Arg Arg Thr Thr Leu
            20                  25                  30

Asn Asn His Asn His Ile Phe Thr Asp Ala Phe Glu Ile Leu Ala Glu
        35                  40                  45

Asn Cys Glu Phe Arg Glu Asn Glu Gly Ser Tyr Val Thr Tyr Met Arg
    50                  55                  60

Ala Ala Ser Val Leu Lys Ser Leu Pro Phe Ser Ile Ile Ser Met Lys
65                  70                  75                  80

Asp Thr Glu Gly Ile Pro Cys Leu Ala Asp Lys Val Lys Cys Val Ile
                85                  90                  95

```
Glu Glu Ile Ile Glu Asp Gly Glu Ser Ser Glu Val Lys Ala Val Leu
                100                 105                 110

Asn Asp Glu Arg Tyr Lys Ser Phe Lys Leu Phe Thr Ser Val Phe Gly
            115                 120                 125

Val Gly Leu Lys Thr Ala Glu Lys Trp Phe Arg Leu Gly Phe Arg Thr
        130                 135                 140

Leu Ser Gly Ile Met Asn Asp Lys Thr Leu Lys Leu Thr His Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Gly Val Leu Val Lys Glu Ala Val Trp Ala
            180                 185                 190

Phe Leu Pro Asp Ala Ile Val Thr Met Thr Gly Gly Phe Arg Arg Gly
        195                 200                 205

Lys Lys Val Gly His Asp Val Asp Phe Leu Ile Thr Ser Pro Glu Ala
210                 215                 220

Thr Glu Glu Gln Glu Gln Gln Leu Leu His Lys Val Ile Thr Phe Trp
225                 230                 235                 240

Glu Lys Glu Gly Leu Leu Leu Tyr Cys Asp Leu Tyr Glu Ser Thr Phe
                245                 250                 255

Glu Lys Leu Lys Met Pro Ser Arg Lys Val Asp Ala Leu Asp His Phe
            260                 265                 270

Gln Lys Cys Phe Leu Ile Leu Lys Leu His Arg Glu Cys Val Asp Asp
        275                 280                 285

Gly Thr Ser Ser Gln Leu Gln Gly Lys Thr Trp Lys Ala Ile Arg Val
290                 295                 300

Asp Leu Val Val Cys Pro Tyr Glu Cys Arg Ala Phe Ala Leu Leu Gly
305                 310                 315                 320

Trp Thr Gly Ser Pro Gln Phe Glu Arg Asp Leu Arg Arg Tyr Ala Thr
                325                 330                 335

His Glu Arg Lys Met Met Leu Asp Asn His Ala Leu Tyr Asp Lys Thr
            340                 345                 350

Lys Arg Lys Phe Leu Ser Ala Asp Ser Glu Glu Asp Ile Phe Ala His
        355                 360                 365

Leu Gly Leu Asp Tyr Ile Glu Pro Trp Glu Arg Asn Ala
370                 375                 380

<210> SEQ ID NO 9
<211> LENGTH: 387
<212> TYPE: PRT
<213> ORGANISM: ARTIFICIAL SEQUENCE
<220> FEATURE:
<223> OTHER INFORMATION: Python truncated

<400> SEQUENCE: 9

Glu Lys Tyr Gln Leu Pro Glu Asp Glu Asp Arg Ser Val Thr Ser Asp
1               5                   10                  15

Leu Asp Arg Asp Ser Ile Ser Glu Tyr Ala Cys Gln Arg Thr Thr
            20                  25                  30

Leu Lys Asn Tyr Asn Gln Lys Phe Thr Asp Ala Phe Glu Ile Leu Ala
        35                  40                  45

Glu Asn Tyr Glu Phe Asn Glu Asn Lys Gly Phe Cys Thr Ala Phe Arg
    50                  55                  60

Arg Ala Ala Ser Val Leu Lys Cys Leu Pro Phe Thr Ile Val Gln Val
65                  70                  75                  80
```

His Asp Ile Glu Gly Val Pro Trp Met Gly Lys Gln Val Lys Gly Ile
                85                  90                  95

Ile Glu Asp Ile Ile Glu Gly Gly Ser Ser Lys Val Lys Ala Val
            100                 105                 110

Leu Asp Asn Glu Asn Tyr Arg Ser Val Lys Leu Phe Thr Ser Val Phe
            115                 120                 125

Gly Val Gly Leu Lys Thr Ser Asp Lys Trp Tyr Arg Met Gly Leu Arg
130                 135                 140

Thr Leu Glu Glu Val Lys Arg Asp Lys Asn Leu Lys Leu Thr Arg Met
145                 150                 155                 160

Gln Lys Ala Gly Phe Leu His Tyr Asp Asp Leu Thr Ser Cys Val Ser
                165                 170                 175

Lys Ala Glu Ala Asp Ala Ala Ser Leu Ile Val Gln Asp Val Val Trp
            180                 185                 190

Lys Ile Val Pro Asn Ala Ile Val Thr Ile Ala Gly Gly Phe Arg Arg
            195                 200                 205

Gly Lys Gln Thr Gly His Asp Val Asp Phe Leu Ile Thr Val Pro Gly
            210                 215                 220

Ser Lys Gln Glu Glu Glu Leu Leu His Thr Val Ile Asp Ile Trp
225                 230                 235                 240

Lys Lys Gln Glu Leu Leu Leu Tyr Tyr Asp Leu Ile Glu Ser Thr Phe
                245                 250                 255

Glu Asp Thr Lys Leu Pro Ser Arg Lys Val Asp Ala Leu Asp His Phe
            260                 265                 270

Gln Lys Cys Phe Ala Ile Leu Lys Val His Lys Glu Arg Glu Asp Lys
            275                 280                 285

Gly Asn Ser Ile Arg Ser Lys Ala Phe Ser Glu Glu Ile Lys Asp
            290                 295                 300

Trp Lys Ala Ile Arg Val Asp Leu Val Val Pro Phe Glu Gln Tyr
305                 310                 315                 320

Ala Phe Ala Leu Leu Gly Trp Thr Gly Ser Thr Gln Phe Glu Arg Asp
                325                 330                 335

Leu Arg Arg Tyr Ala Thr His Glu Lys Lys Met Met Leu Asp Asn His
            340                 345                 350

Ala Leu Tyr Asp Lys Thr Lys Lys Ile Phe Leu Asn Ala Ala Ser Glu
            355                 360                 365

Glu Glu Ile Phe Ala His Leu Gly Leu Asp Tyr Leu Glu Pro Trp Glu
            370                 375                 380

Arg Asn Ala
385

<210> SEQ ID NO 10
<211> LENGTH: 381
<212> TYPE: PRT
<213> ORGANISM: ARTIFICIAL SEQUENCE
<220> FEATURE:
<223> OTHER INFORMATION: truncated dog

<400> SEQUENCE: 10

Asp Tyr Thr Ala Ser Pro Asn Pro Glu Leu Gln Lys Thr Leu Pro Val
1               5                   10                  15

Ala Val Lys Lys Ile Ser Gln Tyr Ala Cys Gln Arg Arg Thr Thr Leu
            20                  25                  30

Asn Asn Tyr Asn Asn Val Phe Thr Asp Ala Phe Glu Val Leu Ala Glu
        35                  40                  45

```
Asn Tyr Glu Phe Arg Glu Asn Glu Val Phe Ser Leu Thr Phe Met Arg
     50                  55                  60

Ala Ala Ser Val Leu Lys Ser Leu Pro Phe Thr Ile Ile Ser Met Lys
 65                  70                  75                  80

Asp Thr Glu Gly Ile Pro Cys Leu Gly Asp Gln Val Lys Cys Ile Ile
                 85                  90                  95

Glu Glu Ile Ile Glu Asp Gly Glu Ser Ser Glu Val Lys Ala Val Leu
             100                 105                 110

Asn Asp Glu Arg Tyr Gln Ser Phe Lys Leu Phe Thr Ser Val Phe Gly
         115                 120                 125

Val Gly Leu Lys Thr Ser Glu Lys Trp Phe Arg Met Gly Phe Arg Thr
130                 135                 140

Leu Ser Lys Ile Lys Ser Asp Lys Ser Leu Lys Phe Thr Pro Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Gly Val Leu Val Lys Glu Ala Val Gly Ala
            180                 185                 190

Phe Leu Pro Asp Ala Phe Val Thr Met Thr Gly Gly Phe Arg Arg Gly
        195                 200                 205

Lys Lys Met Gly His Asp Val Asp Phe Leu Ile Thr Ser Pro Gly Ser
    210                 215                 220

Thr Asp Glu Asp Glu Glu Gln Leu Leu Pro Lys Val Ile Asn Leu Trp
225                 230                 235                 240

Glu Arg Lys Gly Leu Leu Leu Tyr Cys Asp Leu Val Glu Ser Thr Phe
                245                 250                 255

Glu Lys Leu Lys Leu Pro Ser Arg Lys Val Asp Ala Leu Asp His Phe
            260                 265                 270

Gln Lys Cys Phe Leu Ile Leu Lys Leu His His Gln Arg Val Asp Gly
        275                 280                 285

Gly Lys Cys Ser Gln Gln Glu Gly Lys Thr Trp Lys Ala Ile Arg Val
    290                 295                 300

Asp Leu Val Met Cys Pro Tyr Glu Arg Arg Ala Phe Ala Leu Leu Gly
305                 310                 315                 320

Trp Thr Gly Ser Arg Gln Phe Glu Arg Asp Leu Arg Arg Tyr Ala Ser
                325                 330                 335

His Glu Arg Lys Met Ile Leu Asp Asn His Ala Leu Tyr Asp Lys Thr
            340                 345                 350

Lys Lys Ile Phe Leu Lys Ala Glu Ser Glu Glu Ile Phe Ala His
        355                 360                 365

Leu Gly Leu Asp Tyr Ile Glu Pro Trp Glu Arg Asn Ala
370                 375                 380

<210> SEQ ID NO 11
<211> LENGTH: 382
<212> TYPE: PRT
<213> ORGANISM: ARTIFICIAL SEQUENCE
<220> FEATURE:
<223> OTHER INFORMATION: TRUNC MOLE

<400> SEQUENCE: 11

Gly Asp Cys Pro Ala Ser His Asp Ser Ser Pro Gln Lys Thr Glu Ser
 1               5                  10                  15

Ala Ala Val Gln Lys Ile Ser Gln Tyr Ala Cys Gln Arg Arg Thr Thr
             20                  25                  30
```

```
Leu Asn Asn His Asn His Ile Phe Thr Asp Ala Phe Glu Ile Leu Ala
         35                  40                  45

Glu Asn Cys Glu Phe Arg Glu Asn Gly Ser Tyr Val Thr Tyr Met
 50                  55                  60

Arg Ala Ala Ser Val Leu Lys Ser Leu Pro Phe Ser Ile Ile Ser Met
 65                  70                  75                  80

Lys Asp Thr Glu Gly Ile Pro Cys Leu Ala Asp Lys Val Lys Cys Val
                 85                  90                  95

Ile Glu Glu Ile Ile Glu Asp Gly Glu Ser Ser Glu Val Lys Ala Val
                100                 105                 110

Leu Asn Asp Glu Arg Tyr Lys Ser Phe Lys Leu Phe Thr Ser Val Phe
            115                 120                 125

Gly Val Gly Leu Lys Thr Ala Glu Lys Trp Phe Arg Leu Gly Phe Arg
130                 135                 140

Thr Leu Ser Gly Ile Met Asn Asp Lys Thr Leu Lys Leu Thr His Met
145                 150                 155                 160

Gln Lys Ala Gly Phe Leu Tyr Tyr Glu Asp Leu Val Ser Cys Val Thr
                165                 170                 175

Arg Ala Glu Ala Glu Ala Val Gly Val Leu Val Lys Glu Ala Val Trp
                180                 185                 190

Ala Phe Leu Pro Asp Ala Ile Val Thr Met Thr Gly Gly Phe Arg Arg
                195                 200                 205

Gly Lys Lys Val Gly His Asp Val Asp Phe Leu Ile Thr Ser Pro Glu
            210                 215                 220

Ala Thr Glu Glu Gln Glu Gln Leu Leu His Lys Val Ile Thr Phe
225                 230                 235                 240

Trp Glu Lys Glu Gly Leu Leu Leu Tyr Cys Asp Leu Tyr Glu Ser Thr
                245                 250                 255

Phe Glu Lys Leu Lys Met Pro Ser Arg Lys Val Asp Ala Leu Asp His
                260                 265                 270

Phe Gln Lys Cys Phe Leu Ile Leu Lys Leu His Arg Glu Cys Val Asp
            275                 280                 285

Asp Gly Thr Ser Ser Gln Leu Gln Gly Lys Thr Trp Lys Ala Ile Arg
290                 295                 300

Val Asp Leu Val Val Cys Pro Tyr Glu Cys Arg Ala Phe Ala Leu Leu
305                 310                 315                 320

Gly Trp Thr Gly Ser Pro Gln Phe Glu Arg Asp Leu Arg Arg Tyr Ala
                325                 330                 335

Thr His Glu Arg Lys Met Met Leu Asp Asn His Ala Leu Tyr Asp Lys
            340                 345                 350

Thr Lys Arg Lys Phe Leu Ser Ala Asp Ser Glu Glu Asp Ile Phe Ala
        355                 360                 365

His Leu Gly Leu Asp Tyr Ile Glu Pro Trp Glu Arg Asn Ala
    370                 375                 380
```

<210> SEQ ID NO 12
<211> LENGTH: 379
<212> TYPE: PRT
<213> ORGANISM: ARTIFICIAL SEQUENCE
<220> FEATURE:
<223> OTHER INFORMATION: Pika trunk

<400> SEQUENCE: 12

```
Glu Tyr Ser Ala Asn Pro Ser Pro Gly Pro Gln Ala Thr Pro Ala Val
 1               5                  10                  15
```

```
Tyr Lys Ile Ser Gln Tyr Ala Cys Gln Arg Arg Thr Thr Leu Asn Asn
            20                  25                  30

His Asn His Ile Phe Thr Asp Ala Phe Glu Ile Leu Ala Glu Asn Tyr
        35                  40                  45

Glu Phe Lys Glu Asn Glu Gly Cys Tyr Val Thr Tyr Met Arg Ala Ala
50                  55                  60

Ser Val Leu Lys Ser Leu Pro Phe Thr Ile Val Ser Met Lys Asp Thr
65                  70                  75                  80

Glu Gly Ile Pro Cys Leu Glu Asp Lys Val Lys Ser Ile Met Glu Glu
                85                  90                  95

Ile Ile Glu Glu Gly Glu Ser Ser Glu Val Lys Ala Val Leu Ser Asp
            100                 105                 110

Glu Arg Tyr Gln Cys Phe Lys Leu Phe Thr Ser Val Phe Gly Val Gly
        115                 120                 125

Leu Lys Thr Ser Glu Lys Trp Phe Arg Met Gly Phe Arg Ser Leu Ser
130                 135                 140

Asn Ile Arg Leu Asp Lys Ser Leu Lys Phe Thr Gln Met Gln Lys Ala
145                 150                 155                 160

Gly Phe Arg Tyr Tyr Glu Asp Ile Val Ser Cys Val Thr Arg Ala Glu
                165                 170                 175

Ala Glu Ala Val Asp Val Leu Val Asn Glu Ala Val Arg Ala Phe Leu
            180                 185                 190

Pro Asp Ala Phe Ile Thr Met Thr Gly Gly Phe Arg Arg Gly Lys Lys
        195                 200                 205

Ile Gly His Asp Val Asp Phe Leu Ile Thr Ser Pro Glu Leu Thr Glu
210                 215                 220

Glu Asp Glu Gln Gln Leu Leu His Lys Val Met Asn Leu Trp Glu Lys
225                 230                 235                 240

Lys Gly Leu Leu Leu Tyr His Asp Leu Val Glu Ser Thr Phe Glu Lys
                245                 250                 255

Leu Lys Gln Pro Ser Arg Lys Val Asp Ala Leu Asp His Phe Gln Lys
            260                 265                 270

Cys Phe Leu Ile Phe Lys Leu Tyr His Glu Arg Val Gly Gly Asp Arg
        275                 280                 285

Cys Arg Gln Pro Glu Gly Lys Asp Trp Lys Ala Ile Arg Val Asp Leu
290                 295                 300

Val Met Cys Pro Tyr Glu Cys His Ala Phe Ala Leu Leu Gly Trp Thr
305                 310                 315                 320

Gly Ser Arg Gln Phe Glu Arg Asp Leu Arg Arg Tyr Ala Ser His Glu
                325                 330                 335

Arg Lys Met Ile Leu Asp Asn His Ala Leu Tyr Asp Lys Thr Lys Arg
            340                 345                 350

Val Phe Leu Gln Ala Glu Asn Glu Glu Ile Phe Ala His Leu Gly
        355                 360                 365

Leu Asp Tyr Ile Glu Pro Trp Glu Arg Asn Ala
        370                 375

<210> SEQ ID NO 13
<211> LENGTH: 384
<212> TYPE: PRT
<213> ORGANISM: ARTIFICIAL SEQUENCE
<220> FEATURE:
<223> OTHER INFORMATION: TRUNC HEDGEHOG

<400> SEQUENCE: 13
```

```
Asp Ala Ser Phe Gly Ser Asn Pro Gly Ser Gln Asn Thr Pro Pro Leu
1               5                   10                  15

Ala Ile Lys Lys Ile Ser Gln Tyr Ala Cys Gln Arg Arg Thr Ser Leu
            20                  25                  30

Asn Asn Cys Asn His Ile Phe Thr Asp Ala Leu Asp Ile Leu Ala Glu
        35                  40                  45

Asn His Glu Phe Arg Glu Asn Glu Val Ser Cys Val Ala Phe Met Arg
    50                  55                  60

Ala Ala Ser Val Leu Lys Ser Leu Pro Phe Thr Ile Ile Ser Met Lys
65                  70                  75                  80

Asp Thr Lys Gly Ile Pro Cys Leu Gly Asp Lys Ala Lys Cys Val Ile
                85                  90                  95

Glu Glu Ile Ile Glu Asp Gly Glu Ser Ser Glu Val Lys Ala Ile Leu
                100                 105                 110

Asn Asp Glu Arg Tyr Gln Ser Phe Lys Leu Phe Thr Ser Val Phe Gly
            115                 120                 125

Val Gly Leu Lys Thr Ser Glu Lys Trp Phe Arg Met Gly Phe Arg Thr
            130                 135                 140

Leu Asn Lys Ile Met Ser Asp Lys Thr Leu Lys Leu Thr Arg Met Gln
145                 150                 155                 160

Lys Ala Gly Phe Leu Tyr Tyr Glu Asp Leu Val Ser Cys Val Ala Lys
                165                 170                 175

Ala Glu Ala Asp Ala Val Ser Val Leu Val Gln Glu Ala Val Trp Ala
            180                 185                 190

Phe Leu Pro Asp Ala Met Val Thr Met Thr Gly Gly Phe Arg Arg Gly
            195                 200                 205

Lys Lys Leu Gly His Asp Val Asp Phe Leu Ile Thr Ser Pro Gly Ala
210                 215                 220

Thr Glu Glu Glu Glu Gln Gln Leu Leu Pro Lys Val Ile Asn Phe Trp
225                 230                 235                 240

Glu Arg Lys Gly Leu Leu Leu Tyr His Asp Leu Val Glu Ser Thr Phe
            245                 250                 255

Glu Lys Leu Lys Leu Pro Ser Arg Lys Val Asp Ala Leu Asp His Phe
            260                 265                 270

Gln Lys Cys Phe Leu Ile Leu Lys Leu His His Gln His Val Asn Gly
            275                 280                 285

Val Gly Asn Ser Lys Thr Gly Gln Gln Glu Gly Lys Asn Trp Lys Ala
            290                 295                 300

Ile Arg Val Asp Leu Val Met Cys Pro Tyr Glu Arg Arg Ala Phe Ala
305                 310                 315                 320

Leu Leu Gly Trp Thr Gly Ser Arg Gln Phe Glu Arg Asp Leu Arg Arg
            325                 330                 335

Phe Ala Thr His Glu Arg Lys Met Met Leu Asp Asn His Ala Leu Tyr
            340                 345                 350

Asp Lys Thr Lys Arg Ile Phe Leu Lys Ala Glu Ser Glu Glu Glu Ile
            355                 360                 365

Phe Ala His Leu Gly Leu Asp Tyr Ile Asp Pro Trp Glu Arg Asn Ala
            370                 375                 380

<210> SEQ ID NO 14
<211> LENGTH: 381
<212> TYPE: PRT
<213> ORGANISM: ARTIFICIAL SEQUENCE
<220> FEATURE:
<223> OTHER INFORMATION: truncated tree shrew
```

<400> SEQUENCE: 14

```
Asp His Ser Thr Ser Pro Ser Pro Gly Pro Gln Lys Thr Pro Ala Leu
1               5                   10                  15

Ala Val Gln Lys Ile Ser Gln Tyr Ala Cys Gln Arg Arg Thr Thr Leu
            20                  25                  30

Asn Asn Cys Asn Arg Val Phe Thr Asp Ala Phe Glu Thr Leu Ala Glu
        35                  40                  45

Asn Tyr Glu Phe Arg Glu Asn Glu Asp Ser Ser Val Ile Phe Leu Arg
    50                  55                  60

Ala Ala Ser Val Leu Arg Ser Leu Pro Phe Thr Ile Thr Ser Met Arg
65                  70                  75                  80

Asp Thr Glu Gly Leu Pro Cys Leu Gly Asp Lys Val Lys Cys Val Ile
                85                  90                  95

Glu Glu Ile Ile Glu Asp Gly Glu Ser Ser Glu Val Asn Ala Val Leu
                100                 105                 110

Asn Asp Glu Arg Tyr Lys Ser Phe Lys Leu Phe Thr Ser Val Phe Gly
            115                 120                 125

Val Gly Leu Lys Thr Ser Glu Lys Trp Phe Arg Met Gly Phe Arg Thr
130                 135                 140

Leu Ser Arg Val Arg Ser Asp Lys Ser Leu His Leu Thr Arg Met Gln
145                 150                 155                 160

Gln Ala Gly Phe Leu Tyr Tyr Glu Asp Leu Ala Ser Cys Val Thr Arg
                165                 170                 175

Ala Glu Ala Glu Ala Val Gly Val Leu Val Lys Glu Ala Val Gly Ala
            180                 185                 190

Phe Leu Pro Asp Ala Leu Val Thr Ile Thr Gly Gly Phe Arg Arg Gly
        195                 200                 205

Lys Lys Thr Gly His Asp Val Asp Phe Leu Ile Thr Ser Pro Gly Ser
    210                 215                 220

Thr Glu Glu Lys Glu Gly Glu Leu Leu Gln Lys Val Leu Asn Leu Trp
225                 230                 235                 240

Glu Lys Lys Gly Leu Leu Leu Tyr Tyr Asp Leu Val Glu Ser Thr Phe
                245                 250                 255

Glu Lys Leu Lys Thr Pro Ser Arg Lys Val Asp Ala Leu Asp His Phe
            260                 265                 270

Pro Lys Cys Phe Leu Ile Leu Lys Leu His His Gln Arg Val Asp Gly
        275                 280                 285

Asp Lys Pro Ser Gln Gln Glu Gly Lys Ser Trp Lys Ala Ile Arg Val
    290                 295                 300

Asp Leu Val Met Cys Pro Tyr Glu Arg His Ala Phe Ala Leu Leu Gly
305                 310                 315                 320

Trp Thr Gly Ser Arg Gln Phe Glu Arg Asp Leu Arg Arg Tyr Ala Thr
                325                 330                 335

His Glu Arg Lys Met Met Leu Asp Asn His Ala Leu Tyr Asp Lys Thr
            340                 345                 350

Lys Arg Val Phe Leu Lys Ala Glu Ser Glu Glu Asp Ile Phe Ala His
        355                 360                 365

Leu Gly Leu Asp Tyr Ile Glu Pro Trp Glu Arg Asn Ala
    370                 375                 380
```

<210> SEQ ID NO 15
<211> LENGTH: 394
<212> TYPE: PRT

<213> ORGANISM: ARTIFICIAL SEQUENCE
<220> FEATURE:
<223> OTHER INFORMATION: TRUNCATED PLATYPUS

<400> SEQUENCE: 15

```
Leu Thr Asn Ser Ala Pro Ile Asn Cys Met Thr Glu Thr Pro Ser Leu
1               5                   10                  15

Ala Thr Lys Gln Val Ser Gln Tyr Ala Cys Glu Arg Arg Thr Thr Leu
            20                  25                  30

Asn Asn Cys Asn Gln Lys Phe Thr Asp Ala Phe Glu Ile Leu Ala Lys
        35                  40                  45

Asp Phe Glu Phe Arg Glu Asn Glu Gly Ile Cys Leu Ala Phe Met Arg
    50                  55                  60

Ala Ile Ser Val Leu Lys Cys Leu Pro Phe Thr Ile Val Arg Met Lys
65                  70                  75                  80

Asp Ile Glu Gly Val Pro Trp Leu Gly Asp Gln Val Lys Ser Ile Ile
                85                  90                  95

Glu Glu Ile Ile Glu Asp Gly Glu Ser Ser Val Lys Ala Val Leu
            100                 105                 110

Asn Asp Glu Arg Tyr Arg Ser Phe Gln Leu Phe Asn Ser Val Phe Glu
        115                 120                 125

Val Gly Leu Thr Asp Asn Gly Glu Asn Gly Ile Ala Arg Gly Phe Gln
    130                 135                 140

Thr Leu Asn Glu Val Ile Thr Asp Glu Asn Ile Ser Leu Thr Lys Thr
145                 150                 155                 160

Thr Leu Ser Thr Ser Leu Trp Asn Tyr Leu Pro Gly Phe Leu Tyr Tyr
                165                 170                 175

Glu Asp Leu Val Ser Cys Val Ala Lys Glu Glu Ala Asp Ala Val Tyr
            180                 185                 190

Leu Ile Val Lys Glu Ala Val Arg Ala Phe Leu Pro Glu Ala Leu Val
        195                 200                 205

Thr Leu Thr Gly Gly Phe Arg Arg Gly Lys Lys Ile Gly His Asp Val
    210                 215                 220

Asp Phe Leu Ile Ser Asp Pro Glu Ser Gly Gln Asp Glu Gln Leu Leu
225                 230                 235                 240

Pro Asn Ile Ile Lys Leu Trp Glu Lys Gln Glu Leu Leu Tyr Tyr
                245                 250                 255

Asp Leu Val Glu Ser Thr Phe Glu Lys Thr Lys Ile Pro Ser Arg Lys
            260                 265                 270

Val Asp Ala Met Asp His Phe Gln Lys Cys Phe Leu Ile Leu Lys Leu
        275                 280                 285

His His Gln Lys Val Asp Ser Gly Arg Tyr Lys Pro Pro Pro Glu Ser
    290                 295                 300

Lys Asn His Glu Ala Lys Asn Trp Lys Ala Ile Arg Val Asp Leu Val
305                 310                 315                 320

Met Cys Pro Phe Glu Gln Tyr Ala Tyr Ala Leu Leu Gly Trp Thr Gly
                325                 330                 335

Ser Arg Gln Phe Glu Arg Asp Leu Arg Arg Tyr Ala Thr His Glu Lys
            340                 345                 350

Lys Met Met Leu Asp Asn His Ala Leu Tyr Asp Lys Thr Lys Lys Ile
        355                 360                 365

Phe Leu Lys Ala Glu Ser Glu Glu Asp Ile Phe Thr His Leu Gly Leu
    370                 375                 380

Asp Tyr Ile Glu Pro Trp Glu Arg Asn Ala
```

385                390

<210> SEQ ID NO 16
<211> LENGTH: 384
<212> TYPE: PRT
<213> ORGANISM: ARTIFICIAL SEQUENCE
<220> FEATURE:
<223> OTHER INFORMATION: TRUNCATED JERBOA

<400> SEQUENCE: 16

Ser Ser Glu Leu Glu Leu Leu Asp Val Ser Trp Leu Ile Glu Cys Met
1               5                   10                  15

Gly Ala Gly Lys Pro Val Glu Met Thr Gly Arg His Gln Leu Val Lys
            20                  25                  30

Gln Thr Phe Cys Leu Pro Gly Phe Ile Leu Gln Asp Ala Phe Asp Ile
        35                  40                  45

Leu Ala Glu Asn Cys Glu Phe Arg Glu Asn Glu Ala Ser Cys Val Glu
    50                  55                  60

Phe Met Arg Ala Ala Ser Val Leu Lys Ser Leu Pro Phe Pro Ile Ile
65                  70                  75                  80

Ser Val Lys Asp Thr Glu Gly Ile Pro Trp Leu Gly Gly Lys Val Lys
                85                  90                  95

Cys Val Ile Glu Glu Ile Ile Glu Asp Gly Glu Ser Ser Glu Val Lys
            100                 105                 110

Ala Leu Leu Asn Asp Glu Arg Tyr Lys Ser Phe Lys Leu Phe Thr Ser
        115                 120                 125

Val Phe Gly Val Gly Leu Lys Thr Ala Glu Arg Trp Phe Arg Met Gly
    130                 135                 140

Phe Arg Thr Leu Ser Thr Val Lys Leu Asp Lys Ser Leu Thr Phe Thr
145                 150                 155                 160

Arg Met Gln Lys Ala Gly Phe Leu His Tyr Glu Asp Leu Val Ser Cys
                165                 170                 175

Val Thr Arg Ala Glu Ala Glu Ala Val Ser Val Leu Val Gln Gln Ala
            180                 185                 190

Val Val Ala Phe Leu Pro Asp Ala Leu Val Ser Met Thr Gly Gly Phe
        195                 200                 205

Arg Arg Gly Lys Lys Ile Gly His Asp Val Asp Phe Leu Ile Thr Ser
    210                 215                 220

Pro Glu Ala Thr Glu Glu Glu Gln Gln Leu Leu His Lys Val Thr
225                 230                 235                 240

Asn Phe Trp Glu Gln Lys Gly Leu Leu Leu Tyr Cys Asp His Val Glu
                245                 250                 255

Ser Thr Phe Glu Lys Cys Lys Leu Pro Ser Arg Lys Val Asp Ala Leu
            260                 265                 270

Asp His Phe Gln Lys Cys Phe Leu Ile Leu Lys Leu Tyr Arg Glu Arg
        275                 280                 285

Val Asp Ser Val Lys Ser Ser Gln Gln Glu Gly Lys Gly Trp Lys Ala
    290                 295                 300

Ile Arg Val Asp Leu Val Met Cys Pro Tyr Glu Cys Arg Ala Phe Ala
305                 310                 315                 320

Leu Leu Gly Trp Thr Gly Ser Arg Gln Phe Glu Arg Asp Leu Arg Arg
                325                 330                 335

Tyr Ala Thr His Glu Arg Lys Met Arg Leu Asp Asn His Ala Leu Tyr
            340                 345                 350

Asp Lys Thr Lys Arg Val Phe Leu Lys Ala Glu Ser Glu Glu Glu Ile

```
                355                 360                 365
Phe Ala His Leu Gly Leu Glu Tyr Ile Glu Pro Leu Glu Arg Asn Ala
    370                 375                 380

<210> SEQ ID NO 17
<211> LENGTH: 381
<212> TYPE: PRT
<213> ORGANISM: ARTIFICIAL SEQUENCE
<220> FEATURE:
<223> OTHER INFORMATION: Mouse TdT mutant

<400> SEQUENCE: 17

Ser Gly Ser Pro Ser Pro Val Pro Gly Ser Gln Asn Val Pro Ala Pro
1               5                   10                  15

Val Val Lys Lys Ile Ser Gln Tyr Ala Cys Gln Arg Arg Thr Thr Leu
            20                  25                  30

Asn Asn Tyr Asn Gln Leu Phe Thr Asp Ala Leu Asp Ile Leu Ala Glu
        35                  40                  45

Asn Asp Glu Phe Arg Glu Asn Glu Glu Ser Cys Leu Ala Phe Arg Arg
    50                  55                  60

Ala Ser Ser Val Leu Lys Ser Leu Pro Phe Pro Ile Thr Ser Met Lys
65                  70                  75                  80

Asp Thr Glu Gly Ile Pro Cys Leu Gly Asp Lys Val Lys Ser Ile Ile
                85                  90                  95

Glu Gly Ile Ile Glu Asp Gly Glu Ser Ser Glu Val Lys Ala Val Leu
            100                 105                 110

Asn Asp Glu Arg Tyr Lys Ser Phe Lys Leu Phe Thr Ser Val Phe Gly
        115                 120                 125

Val Gly Leu Lys Thr Ala Glu Lys Trp Phe Arg Met Gly Phe Arg Thr
    130                 135                 140

Leu Ser Lys Ile Gln Ser Asp Lys Ser Leu Arg Phe Thr Gln Met Gln
145                 150                 155                 160

Lys Ala Gly Phe Leu Tyr Tyr Glu Asp Leu Val Ser Gly Val Asn Arg
                165                 170                 175

Pro Glu Ala Glu Ala Val Ser Met Leu Val Lys Glu Ala Val Val Thr
            180                 185                 190

Phe Leu Pro Asp Ala Leu Val Thr Met Thr Gly Gly Phe Arg Leu Gly
        195                 200                 205

Lys Met Thr Gly His Asp Val Asp Phe Leu Ile Thr Ser Pro Glu Ala
    210                 215                 220

Thr Glu Asp Glu Glu Gln Gln Leu Leu His Lys Val Thr Asp Phe Trp
225                 230                 235                 240

Lys Gln Gln Gly Leu Leu Leu Tyr Cys Asp Ile Leu Glu Ser Thr Phe
                245                 250                 255

Glu Lys Phe Lys Gln Pro Ser Arg Thr Val Asp Ala Leu Asp His Phe
            260                 265                 270

Gln Lys Cys Phe Leu Ile Leu Lys Leu Asp His Pro Arg Val His Ser
        275                 280                 285

Val Lys Ser Gly Gln Gln Glu Gly Lys Gly Trp Lys Ala Ile Arg Val
    290                 295                 300

Asp Leu Val Met Cys Pro Tyr Asp Arg Arg Ala Phe Ala Leu Leu Gly
305                 310                 315                 320

Trp Thr Gly Ser Pro Gln Phe Asn Arg Asp Leu Arg Arg Tyr Ala Thr
                325                 330                 335

His Glu Arg Lys Met Met Leu Asp Asn His Ala Leu Tyr Asp Lys Thr
```

```
                340                 345                 350
Lys Arg Val Phe Leu Glu Ala Glu Ser Glu Glu Ile Phe Ala His
            355                 360                 365

Leu Gly Leu Asp Tyr Ile Glu Pro Trp Glu Arg Asn Ala
    370                 375                 380

<210> SEQ ID NO 18
<211> LENGTH: 381
<212> TYPE: PRT
<213> ORGANISM: ARTIFICIAL SEQUENCE
<220> FEATURE:
<223> OTHER INFORMATION: Mouse TdT mutant

<400> SEQUENCE: 18

Ser Gly Ser Pro Ser Pro Val Pro Gly Ser Gln Asn Val Pro Ala Pro
1               5                   10                  15

Val Val Lys Lys Ile Ser Gln Tyr Ala Cys Gln Arg Arg Thr Thr Leu
                20                  25                  30

Asn Asn Tyr Asn Glu Leu Phe Thr Arg Ala Leu Asp Ile Leu Ala Glu
            35                  40                  45

Asn Asp Glu Phe Arg Glu Asn Glu Glu Ser Arg Asp Ala Phe Arg Arg
50                  55                  60

Ala Ser Ser Val Leu Lys Ser Leu Pro Phe Pro Ile Thr Ser Met Lys
65                  70                  75                  80

Asp Thr Glu Gly Ile Pro Cys Leu Gly Asp Lys Val Lys Arg Ile Ile
                85                  90                  95

Glu Glu Ile Ile Glu Asp Gly Glu Ser Ser Glu Val Lys Ala Val Leu
            100                 105                 110

Asn Asp Glu Arg Tyr Gln Ala Phe Lys Leu Phe Thr Ser Val Phe Gly
        115                 120                 125

Val Gly Arg Lys Thr Ala Glu Lys Trp Phe Arg Met Gly Phe Arg Thr
130                 135                 140

Leu Glu Lys Ile Arg Ser Asp Lys Ser Leu Arg Phe Thr Gln Met Gln
145                 150                 155                 160

Lys Ala Gly Phe Leu Tyr Tyr Glu Asp Leu Val Ser Gly Val Asn Arg
                165                 170                 175

Pro Glu Ala Glu Ala Val Ser Met Leu Val Lys Glu Ala Val Val Thr
            180                 185                 190

Phe Leu Pro Asp Ala Leu Val Thr Met Thr Gly Gly Phe Arg Leu Gly
        195                 200                 205

Lys Met Thr Gly His Asp Val Asp Phe Leu Ile Thr Ser Pro Glu Ala
210                 215                 220

Thr Glu Asp Glu Glu Gln Gln Leu Leu His Lys Val Thr Asp Phe Trp
225                 230                 235                 240

Lys Gln Gln Gly Leu Leu Leu Tyr Cys Asp Ile Leu Glu Ser Thr Phe
                245                 250                 255

Glu Lys Phe Lys Gln Pro Ser Arg Thr Val Asp Ala Leu Asp His Phe
            260                 265                 270

Gln Lys Cys Phe Leu Ile Leu Lys Leu Asp His Pro Arg Val His Ser
        275                 280                 285

Val Lys Ser Gly Gln Gln Glu Gly Lys Gly Trp Lys Ala Ile Arg Val
290                 295                 300

Asp Leu Val Met Cys Pro Tyr Asp Arg Arg Ala Phe Ala Leu Leu Gly
305                 310                 315                 320

Trp Thr Gly Ser Ala Phe Phe Asn Arg Asp Leu Arg Arg Tyr Ala Thr
```

```
                    325                 330                 335
His Glu Arg Lys Met Met Leu Asp Asn His Ala Leu Tyr Asp Lys Thr
                340                 345                 350
Lys Arg Val Phe Leu Glu Ala Glu Ser Glu Glu Ile Phe Ala His
            355                 360                 365
Leu Gly Leu Asp Tyr Ile Glu Pro Arg Glu Arg Asn Ala
        370                 375                 380

<210> SEQ ID NO 19
<211> LENGTH: 381
<212> TYPE: PRT
<213> ORGANISM: ARTIFICIAL SEQUENCE
<220> FEATURE:
<223> OTHER INFORMATION: Mouse TdT mutant

<400> SEQUENCE: 19

Ser Gly Ser Pro Ser Pro Val Pro Gly Ser Gln Asn Val Pro Ala Pro
1               5                  10                  15
Val Val Lys Lys Ile Ser Gln Tyr Ala Cys Gln Arg Arg Thr Thr Leu
            20                  25                  30
Asn Asn Tyr Asn Glu Leu Phe Thr Arg Ala Leu Asp Ile Leu Ala Glu
        35                  40                  45
Asn Asp Glu Phe Arg Glu Asn Glu Glu Ser Arg Asp Ala Phe Arg Arg
    50                  55                  60
Ala Ser Ser Val Leu Lys Ser Leu Pro Phe Pro Ile Thr Ser Met Lys
65                  70                  75                  80
Asp Thr Glu Gly Ile Pro Cys Leu Gly Asp Lys Val Lys Arg Ile Ile
                85                  90                  95
Glu Glu Ile Ile Glu Asp Gly Glu Ser Ser Glu Val Lys Ala Val Leu
            100                 105                 110
Asn Asp Glu Arg Tyr Lys Ala Phe Lys Leu Phe Thr Ser Val Phe Gly
        115                 120                 125
Val Gly Arg Lys Thr Ala Glu Lys Trp Phe Arg Met Gly Phe Arg Thr
    130                 135                 140
Leu Glu Lys Ile Arg Ser Asp Lys Ser Leu Arg Phe Thr Gln Met Gln
145                 150                 155                 160
Lys Ala Gly Phe Leu Tyr Tyr Glu Asp Leu Val Ser Gly Val Asn Arg
                165                 170                 175
Pro Glu Ala Glu Ala Val Ser Met Leu Val Lys Glu Ala Val Val Thr
            180                 185                 190
Phe Leu Pro Asp Ala Leu Val Thr Met Thr Gly Gly Phe Arg Leu Gly
        195                 200                 205
Lys Met Thr Gly His Asp Val Asp Phe Leu Ile Thr Ser Pro Glu Ala
    210                 215                 220
Thr Glu Asp Glu Glu Gln Gln Leu Leu His Lys Val Thr Asp Phe Trp
225                 230                 235                 240
Lys Gln Gln Gly Leu Leu Leu Tyr Cys Asp Ile Leu Glu Ser Thr Phe
                245                 250                 255
Glu Lys Phe Lys Gln Pro Ser Arg Thr Val Asp Ala Leu Asp His Phe
            260                 265                 270
Gln Lys Cys Phe Leu Ile Leu Lys Leu Asp His Pro Arg Val His Ser
        275                 280                 285
Val Lys Ser Gly Gln Gln Glu Gly Lys Gly Trp Lys Ala Ile Arg Val
    290                 295                 300
Asp Leu Val Met Cys Pro Tyr Asp Arg Arg Ala Phe Ala Leu Leu Gly
```

```
                    305                 310                 315                 320
Trp Thr Gly Ser Ala Phe Phe Asn Arg Asp Leu Arg Arg Tyr Ala Thr
                325                 330                 335

His Glu Arg Lys Met Met Leu Asp Asn His Ala Leu Tyr Asp Lys Thr
                340                 345                 350

Lys Arg Val Phe Leu Glu Ala Glu Ser Glu Glu Ile Phe Ala His
                355                 360                 365

Leu Gly Leu Asp Tyr Ile Glu Pro Trp Glu Arg Asn Ala
                370                 375                 380

<210> SEQ ID NO 20
<211> LENGTH: 381
<212> TYPE: PRT
<213> ORGANISM: ARTIFICIAL SEQUENCE
<220> FEATURE:
<223> OTHER INFORMATION: Mouse TdT mutant

<400> SEQUENCE: 20

Ser Gly Ser Pro Ser Pro Val Pro Gly Ser Gln Asn Val Pro Ala Pro
1               5                   10                  15

Val Val Lys Lys Ile Ser Gln Tyr Ala Cys Gln Arg Arg Thr Thr Leu
                20                  25                  30

Asn Asn Tyr Asn Glu Leu Phe Thr Arg Ala Leu Asp Ile Leu Ala Glu
                35                  40                  45

Asn Asp Glu Phe Arg Glu Asn Glu Ser Cys Leu Ala Phe Arg Arg
    50                  55                  60

Ala Ser Ser Val Leu Lys Ser Leu Pro Phe Pro Ile Thr Ser Met Lys
65                  70                  75                  80

Asp Thr Glu Gly Ile Pro Cys Leu Gly Asp Lys Val Lys Arg Ile Ile
                85                  90                  95

Glu Glu Ile Ile Glu Asp Gly Glu Ser Ser Glu Val Lys Ala Val Leu
                100                 105                 110

Asn Asp Glu Arg Tyr Lys Ser Phe Lys Leu Phe Thr Ser Val Phe Gly
                115                 120                 125

Val Gly Leu Lys Thr Ala Glu Lys Trp Phe Arg Met Gly Phe Arg Thr
                130                 135                 140

Leu Glu Lys Ile Arg Ser Asp Lys Ser Leu Arg Phe Thr Gln Met Gln
145                 150                 155                 160

Lys Ala Gly Phe Leu Tyr Tyr Glu Asp Leu Val Ser Gly Val Asn Arg
                165                 170                 175

Pro Glu Ala Glu Ala Val Ser Thr Leu Val Lys Glu Ala Val Val Thr
                180                 185                 190

Phe Leu Pro Asp Ala Leu Val Thr Met Thr Gly Gly Phe Arg Leu Gly
                195                 200                 205

His Met Thr Gly His Asp Val Asp Phe Leu Ile Thr Ser Pro Glu Ala
                210                 215                 220

Thr Glu Asp Glu Glu Gln Gln Leu Leu His Lys Val Thr Asp Phe Trp
225                 230                 235                 240

Lys Gln Gln Gly Leu Leu Leu Tyr Cys Asp Ile Leu Glu Ser Thr Phe
                245                 250                 255

Glu Lys Phe Lys Gln Pro Ser Arg Lys Val Asp Ala Leu Asp His Phe
                260                 265                 270

Gln Lys Cys Phe Leu Ile Leu Lys Leu Asp His Leu Arg Val His Ser
                275                 280                 285

Ala Lys Ser Gly Gln Gln Glu Gly Lys Gly Trp Lys Ala Ile Arg Val
```

```
                    290                 295                 300
Asp Leu Val Met Cys Pro Tyr Asp Arg Arg Ala Phe Ala Leu Leu Gly
305                 310                 315                 320

Trp Thr Gly Ser Val Gln Phe Lys Arg Asp Leu Arg Arg Tyr Ala Thr
                325                 330                 335

His Glu Arg Lys Met Met Leu Asp Glu His Ala Leu Tyr Asp Lys Thr
            340                 345                 350

Lys Arg Val Phe Leu Glu Ala Glu Ser Glu Glu Glu Ile Phe Ala His
        355                 360                 365

Leu Gly Leu Asp Tyr Ile Glu Pro Trp Glu Arg Asn Ala
    370                 375                 380

<210> SEQ ID NO 21
<211> LENGTH: 12
<212> TYPE: DNA
<213> ORGANISM: ARTIFICIAL SEQUENCE
<220> FEATURE:
<223> OTHER INFORMATION: Test Polynucleotide p875

<400> SEQUENCE: 21
cagttaaaaa ct                                                             12

<210> SEQ ID NO 22
<211> LENGTH: 11
<212> TYPE: DNA
<213> ORGANISM: ARTIFICIAL SEQUENCE
<220> FEATURE:
<223> OTHER INFORMATION: Test Polynucleotide p876

<400> SEQUENCE: 22
gagttaaaac t                                                              11

<210> SEQ ID NO 23
<211> LENGTH: 10
<212> TYPE: DNA
<213> ORGANISM: ARTIFICIAL SEQUENCE
<220> FEATURE:
<223> OTHER INFORMATION: Test Polynucleotide p877

<400> SEQUENCE: 23
cagcaaggct                                                                10

<210> SEQ ID NO 24
<211> LENGTH: 364
<212> TYPE: PRT
<213> ORGANISM: ARTIFICIAL SEQUENCE
<220> FEATURE:
<223> OTHER INFORMATION: TdT(Puma wildtype)

<400> SEQUENCE: 24

Val Val Lys Lys Ile Pro Leu Tyr Ala Cys Gln Arg Arg Thr Thr Leu
1               5                   10                  15

Asn Asn Phe Asn His Ile Phe Thr Asp Ala Phe Glu Val Leu Ala Glu
            20                  25                  30

Asn Tyr Glu Phe Lys Glu Asn Glu Ile Ser Ser Ala Thr Phe Met Arg
        35                  40                  45

Ala Ala Ser Val Leu Lys Leu Pro Phe Thr Ile Ile Ser Met Lys Asp
    50                  55                  60

Thr Glu Gly Ile Pro Cys Leu Gly Asp Lys Val Lys Cys Val Ile Glu
65                  70                  75                  80

Glu Ile Ile Glu Asp Gly Glu Ser Ser Glu Val Lys Ala Val Leu Asn
```

```
                85                  90                  95
Asp Glu Arg Tyr Gln Ser Phe Lys Leu Phe Thr Ser Val Phe Gly Val
            100                 105                 110

Gly Leu Lys Thr Ser Glu Lys Trp Phe Arg Met Gly Phe Arg Thr Leu
        115                 120                 125

Ser Lys Ile Lys Ser Asp Lys Thr Leu Lys Phe Thr Gln Met Gln Lys
    130                 135                 140

Ala Gly Phe Leu Tyr Tyr Glu Asp Leu Val Ser Cys Val Thr Arg Ala
145                 150                 155                 160

Glu Ala Glu Ala Val Gly Val Leu Val Lys Glu Ala Val Trp Ala Phe
                165                 170                 175

Leu Pro Asp Ala Phe Val Thr Met Thr Gly Gly Phe Arg Arg Gly Lys
            180                 185                 190

Lys Ile Gly His Asp Val Asp Phe Leu Ile Thr Ile Pro Gly Ser Thr
        195                 200                 205

Asp Glu Glu Glu Glu Gln Leu Leu Pro Lys Val Ile Asn Leu Trp Gln
    210                 215                 220

Arg Lys Glu Leu Leu Leu Tyr Tyr Asp Leu Val Glu Ser Thr Phe Glu
225                 230                 235                 240

Lys Leu Lys Leu Pro Ser Arg Lys Val Asp Ala Leu Asp His Phe Gln
                245                 250                 255

Lys Cys Phe Leu Ile Leu Lys Leu His His Gln Arg Val Asp Ser Gly
            260                 265                 270

Lys Cys Ser Gln Gln Glu Gly Lys Thr Trp Lys Ala Ile Arg Val Asp
        275                 280                 285

Leu Val Met Cys Pro Tyr Glu Arg Arg Ala Phe Ala Leu Leu Gly Trp
    290                 295                 300

Thr Gly Ser Arg Gln Phe Glu Arg Asp Leu Arg Arg Tyr Ala Thr His
305                 310                 315                 320

Glu Arg Lys Met Ile Leu Asp Asn His Ala Leu Tyr Asp Lys Thr Lys
                325                 330                 335

Lys Ile Phe Leu Lys Ala Glu Ser Glu Glu Glu Ile Phe Ala His Leu
            340                 345                 350

Gly Leu Asp Tyr Ile Glu Pro Trp Glu Arg Asn Ala
        355                 360

<210> SEQ ID NO 25
<211> LENGTH: 362
<212> TYPE: PRT
<213> ORGANISM: ARTIFICIAL SEQUENCE
<220> FEATURE:
<223> OTHER INFORMATION: wild type N139 reptilian

<400> SEQUENCE: 25

Tyr Ala Cys Gln Arg Arg Thr Thr Leu Asn Asn Tyr Asn Lys Lys Tyr
1               5                   10                  15

Thr Asp Ala Phe Glu Ile Leu Ala Glu Asn Tyr Glu Met Arg Glu Asn
            20                  25                  30

Ala Gly Ala Cys Leu Ala Phe Arg Arg Ala Ala Ser Val Leu Lys Phe
        35                  40                  45

Leu Pro Phe Ala Ile Val Arg Ser Asn Asp Ile Glu Gly Leu Pro Trp
    50                  55                  60

Met Gly Glu Gln Val Lys Gly Ile Ile Glu Asp Ile Leu Glu Glu Gly
65                  70                  75                  80

Gln Ser Pro Lys Val Glu Ala Val Leu Asn Asn Glu Lys Tyr Arg Ser
```

```
                        85                  90                  95
Phe Lys Leu Phe Thr Ser Val Phe Gly Val Ala Leu Lys Thr Ser Glu
            100                 105                 110

Lys Trp Phe Met Met Gly Leu Arg Asn Leu Glu Asp Val Lys Leu Asn
        115                 120                 125

Gln Asn Leu Gln Leu Thr Arg Met Gln Lys Ala Gly Leu Gln His Tyr
    130                 135                 140

Glu Asp Leu Ile Ser Tyr Val Ser Lys Ala Glu Ala Asp Ser Thr Ser
145                 150                 155                 160

Leu Met Val Lys Asp Thr Val Trp Lys Phe Ser Pro Ser Ala Leu Val
                165                 170                 175

Thr Leu Thr Gly Gly Phe Arg Gly Lys Lys Met Gly His Asp Val
            180                 185                 190

Asp Phe Leu Ile Thr Val Pro Gly Ser Arg Pro Asn Glu Glu Leu Leu
        195                 200                 205

His Leu Val Ile Asp Cys Trp Lys Lys Gln Gly Leu Leu Leu Tyr Tyr
    210                 215                 220

Asp Leu Ile Glu Ser Thr Phe Glu Lys Ser Lys Leu Pro Ser Gln Arg
225                 230                 235                 240

Val Asp Ala Leu Asp His Phe Gln Lys Cys Phe Ala Ile Leu Lys Leu
                245                 250                 255

His Lys Glu Arg Val Asn Gln Gly Thr Ser Leu Pro Pro Val Ala Ser
            260                 265                 270

Thr Val Glu Glu Ile Lys Asp Trp Lys Ala Ile Arg Val Asp Leu Val
        275                 280                 285

Val Ser Pro Phe Glu Gln His Ala Phe Ala Leu Leu Gly Trp Thr Gly
    290                 295                 300

Ser Arg Gln Phe Glu Arg Asp Leu Arg Arg Tyr Ala Thr His Glu Lys
305                 310                 315                 320

Lys Met Met Leu Asp Asn His Ala Leu Tyr Asp Lys Thr Lys Lys Ile
                325                 330                 335

Phe Leu Ser Ala Ser Ser Glu Glu Ile Phe Ala His Leu Gly Leu
            340                 345                 350

Asp Tyr Leu Glu Pro Trp Glu Arg Asn Ala
        355                 360

<210> SEQ ID NO 26
<211> LENGTH: 364
<212> TYPE: PRT
<213> ORGANISM: ARTIFICIAL SEQUENCE
<220> FEATURE:
<223> OTHER INFORMATION: truncated shrew

<400> SEQUENCE: 26

Val Gln Lys Ile Ser Gln Tyr Ala Cys Gln Arg Arg Thr Thr Leu Asn
1               5                   10                  15

Asn His Asn His Ile Phe Thr Asp Ala Phe Glu Ile Leu Ala Glu Asn
                20                  25                  30

Cys Glu Phe Arg Glu Asn Glu Gly Ser Tyr Val Thr Tyr Met Arg Ala
            35                  40                  45

Ala Ser Val Leu Lys Ser Leu Pro Phe Ser Ile Ile Ser Met Lys Asp
        50                  55                  60

Thr Glu Gly Ile Pro Cys Leu Ala Asp Lys Val Lys Cys Val Ile Glu
65                  70                  75                  80

Glu Ile Ile Glu Asp Gly Glu Ser Ser Glu Val Lys Ala Val Leu Asn
```

```
                         85                  90                  95
Asp Glu Arg Tyr Lys Ser Phe Lys Leu Phe Thr Ser Val Phe Gly Val
            100                 105                 110
Gly Leu Lys Thr Ala Glu Lys Trp Phe Arg Leu Gly Phe Arg Thr Leu
        115                 120                 125
Ser Gly Ile Met Asn Asp Lys Thr Leu Lys Leu Thr His Met Gln Lys
        130                 135                 140
Ala Gly Phe Leu Tyr Tyr Glu Asp Leu Val Ser Cys Val Thr Arg Ala
145                 150                 155                 160
Glu Ala Glu Ala Val Gly Val Leu Val Lys Glu Ala Val Trp Ala Phe
                165                 170                 175
Leu Pro Asp Ala Ile Val Thr Met Thr Gly Gly Phe Arg Arg Gly Lys
            180                 185                 190
Lys Val Gly His Asp Val Asp Phe Leu Ile Thr Ser Pro Glu Ala Thr
        195                 200                 205
Glu Glu Gln Glu Gln Gln Leu Leu His Lys Val Ile Thr Phe Trp Glu
        210                 215                 220
Lys Glu Gly Leu Leu Leu Tyr Cys Asp Leu Tyr Glu Ser Thr Phe Glu
225                 230                 235                 240
Lys Leu Lys Met Pro Ser Arg Lys Val Asp Ala Leu Asp His Phe Gln
                245                 250                 255
Lys Cys Phe Leu Ile Leu Lys Leu His Arg Glu Cys Val Asp Asp Gly
            260                 265                 270
Thr Ser Ser Gln Leu Gln Gly Lys Thr Trp Lys Ala Ile Arg Val Asp
        275                 280                 285
Leu Val Val Cys Pro Tyr Glu Cys Arg Ala Phe Ala Leu Leu Gly Trp
        290                 295                 300
Thr Gly Ser Pro Gln Phe Glu Arg Asp Leu Arg Arg Tyr Ala Thr His
305                 310                 315                 320
Glu Arg Lys Met Met Leu Asp Asn His Ala Leu Tyr Asp Lys Thr Lys
                325                 330                 335
Arg Lys Phe Leu Ser Ala Asp Ser Glu Glu Asp Ile Phe Ala His Leu
            340                 345                 350
Gly Leu Asp Tyr Ile Glu Pro Trp Glu Arg Asn Ala
        355                 360

<210> SEQ ID NO 27
<211> LENGTH: 369
<212> TYPE: PRT
<213> ORGANISM: ARTIFICIAL SEQUENCE
<220> FEATURE:
<223> OTHER INFORMATION: BOVINE

<400> SEQUENCE: 27

Lys Thr Pro Pro Leu Val Val Lys Lys Ile Ser Gln Tyr Ala Cys Gln
1               5                   10                  15
Arg Lys Thr Thr Leu Asn Asn Tyr Asn Glu Ile Phe Thr Arg Ala Phe
            20                  25                  30
Glu Ile Leu Ala Glu Asn Ser Glu Phe Lys Glu Asn Glu Glu Ser Tyr
        35                  40                  45
Val Thr Phe Arg Arg Ala Ala Ser Val Leu Lys Ser Leu Pro Phe Thr
        50                  55                  60
Ile Ile Ser Met Lys Asp Thr Glu Gly Ile Pro Cys Leu Gly Asp Lys
65                  70                  75                  80
Val Lys Arg Ile Ile Glu Glu Ile Ile Glu Asp Gly Glu Ser Ser Glu
```

```
            85                  90                  95
Val Lys Ala Val Leu Asn Asp Glu Arg Tyr Gln Ala Phe Lys Leu Phe
            100                 105                 110

Thr Ser Val Phe Gly Val Gly Arg Lys Thr Ser Glu Lys Trp Phe Arg
            115                 120                 125

Met Gly Phe Arg Ser Leu Glu Lys Ile Arg Ser Asp Lys Thr Leu Lys
            130                 135                 140

Phe Thr Lys Met Gln Lys Ala Gly Phe Leu Tyr Tyr Glu Asp Leu Val
145                 150                 155                 160

Ser Gly Val Thr Arg Ala Glu Ala Glu Ala Val Gly Val Leu Val Lys
                165                 170                 175

Glu Ala Val Trp Ala Phe Leu Pro Asp Ala Phe Val Thr Met Thr Gly
                180                 185                 190

Gly Phe Arg Leu Gly Lys Lys Ile Gly His Asp Val Asp Phe Leu Ile
                195                 200                 205

Thr Ser Pro Gly Ser Ala Glu Asp Glu Glu Gln Leu Leu Pro Lys Val
            210                 215                 220

Ile Asn Leu Trp Glu Lys Lys Gly Leu Leu Leu Tyr Tyr Asp Leu Val
225                 230                 235                 240

Glu Ser Thr Phe Glu Lys Phe Lys Leu Pro Ser Arg Gln Val Asp Thr
                245                 250                 255

Leu Asp His Phe Gln Lys Cys Phe Leu Ile Leu Lys Leu His His Gln
                260                 265                 270

Arg Val Asp Ser Ser Lys Ser Asn Gln Gln Glu Gly Lys Thr Trp Lys
            275                 280                 285

Ala Ile Arg Val Asp Leu Val Met Cys Pro Tyr Glu Asn Arg Ala Phe
            290                 295                 300

Ala Leu Leu Gly Trp Thr Gly Ser Ala Phe Phe Asn Arg Asp Ile Arg
305                 310                 315                 320

Arg Tyr Ala Thr His Glu Arg Lys Met Met Leu Asp Asn His Ala Leu
                325                 330                 335

Tyr Asp Lys Thr Lys Arg Val Phe Leu Lys Ala Glu Ser Glu Glu Glu
                340                 345                 350

Ile Phe Ala His Leu Gly Leu Asp Tyr Ile Glu Pro Arg Glu Arg Asn
            355                 360                 365

Ala

<210> SEQ ID NO 28
<211> LENGTH: 374
<212> TYPE: PRT
<213> ORGANISM: ARTIFICIAL SEQUENCE
<220> FEATURE:
<223> OTHER INFORMATION: LATMERIA

<400> SEQUENCE: 28

Asn Val Pro Ala Pro Ser Val Val Ala Ile Ser Gln Tyr Ala Cys Gln
1               5                   10                  15

Arg Arg Thr Thr Leu Asn Asn His Asn Lys Ile Phe Thr Asp Ala Phe
            20                  25                  30

Glu Ile Leu Ala Glu Asn Tyr Glu Phe Asn Gly Asn Glu Gly Pro Cys
            35                  40                  45

Leu Ala Phe Arg Arg Ala Ala Ser Leu Leu Lys Ser Leu Pro Tyr Ala
            50                  55                  60

Ile Ser Ser Met Lys Asp Leu Glu Gly Leu Pro Cys Leu Gly Asp Gln
65                  70                  75                  80
```

```
Thr Lys Ala Val Ile Glu Ile Leu Glu Glu Gly Gln Ser Ser Lys
                85                  90                  95

Val Gln Asp Val Leu Ser Asp Glu Arg Tyr Lys Ser Ile Lys Leu Phe
            100                 105                 110

Thr Ser Val Phe Gly Val Gly Leu Lys Thr Ala Glu Lys Trp Tyr Arg
        115                 120                 125

Lys Gly Phe Arg Thr Leu Glu Glu Val Gln Ala Asp Lys Glu Ile Lys
130                 135                 140

Leu Thr Lys Met Gln Lys Ala Gly Phe Leu Tyr Tyr Glu Asp Ile Ser
145                 150                 155                 160

Ser Ala Val Thr Lys Ala Glu Ala Glu Ala Ile Gly Gln Ile Ile Glu
                165                 170                 175

Asp Thr Val Arg Leu Phe Ala Pro Asp Ala Ile Val Thr Leu Thr Gly
            180                 185                 190

Gly Phe Arg Leu Gly Lys Lys Ile Gly His Asp Val Asp Phe Leu Ile
        195                 200                 205

Thr Thr Pro Glu Thr Gly Asn Glu Asn Gly Leu Leu His Lys Val Ile
210                 215                 220

Asn Val Leu Gln Asn Gln Gly Ile Leu Leu Tyr Tyr Asp Ile Val Glu
225                 230                 235                 240

Ser Thr Phe Asp Lys Thr Arg Leu Pro Ser Arg Lys Val Asp Ala Leu
                245                 250                 255

Asp His Phe Gln Lys Cys Phe Ala Ile Leu Lys Leu His Lys Gln Lys
            260                 265                 270

Val Asn Thr Ser Asn Ser Glu Glu Ala Glu Glu Pro Ser Asn Thr Glu
        275                 280                 285

Thr Lys Asp Trp Lys Ala Ile Arg Val Asp Leu Val Ile Thr Pro Phe
290                 295                 300

Asp Gln Tyr Ala Phe Ala Leu Leu Gly Trp Thr Gly Ser Ala Phe Phe
305                 310                 315                 320

Asn Arg Asp Leu Arg Arg Phe Ala Thr His Glu Arg Lys Met Met Leu
                325                 330                 335

Asp Asn His Ala Leu Tyr Asp Lys Thr Lys Ile Phe Leu Pro Ala
            340                 345                 350

Lys Thr Glu Glu Asp Ile Phe His Leu Gly Leu Asp Tyr Ile Glu
        355                 360                 365

Pro Trp Glu Arg Asn Ala
    370

<210> SEQ ID NO 29
<211> LENGTH: 370
<212> TYPE: PRT
<213> ORGANISM: ARTIFICIAL SEQUENCE
<220> FEATURE:
<223> OTHER INFORMATION: PUMA

<400> SEQUENCE: 29

Lys Thr Glu Ser Ala Val Val Lys Lys Ile Pro Leu Tyr Ala Cys Gln
1               5                   10                  15

Arg Arg Thr Thr Leu Asn Asn Phe Asn Glu Ile Phe Thr Arg Ala Phe
            20                  25                  30

Glu Val Leu Ala Glu Asn Tyr Glu Phe Lys Glu Asn Glu Ile Ser Ser
        35                  40                  45

Ala Thr Phe Arg Arg Ala Ala Ser Val Leu Lys Ser Leu Pro Phe Thr
    50                  55                  60
```

Ile Ile Ser Met Lys Asp Thr Glu Gly Ile Pro Cys Leu Gly Asp Lys
65                  70                  75                  80

Val Lys Arg Val Ile Glu Ile Ile Glu Asp Gly Glu Ser Ser Glu
                85                  90                  95

Val Lys Ala Val Leu Asn Asp Glu Arg Tyr Gln Ala Phe Lys Leu Phe
                100                 105                 110

Thr Ser Val Phe Gly Val Gly Leu Lys Thr Ser Glu Lys Trp Phe Arg
                115                 120                 125

Met Gly Phe Arg Thr Leu Glu Lys Ile Lys Ser Asp Lys Thr Leu Lys
                130                 135                 140

Phe Thr Gln Met Gln Lys Ala Gly Phe Leu Tyr Tyr Glu Asp Leu Val
145                 150                 155                 160

Ser Gly Val Thr Arg Ala Glu Ala Glu Ala Val Gly Val Leu Val Lys
                165                 170                 175

Glu Ala Val Trp Ala Phe Leu Pro Asp Ala Phe Val Thr Met Thr Gly
                180                 185                 190

Gly Phe Arg Leu Gly Lys Lys Ile Gly His Asp Val Asp Phe Leu Ile
                195                 200                 205

Thr Ile Pro Gly Ser Thr Asp Glu Glu Glu Gln Leu Leu Pro Lys
210                 215                 220

Val Ile Asn Leu Trp Gln Arg Lys Glu Leu Leu Leu Tyr Tyr Asp Leu
225                 230                 235                 240

Val Glu Ser Thr Phe Glu Lys Leu Lys Leu Pro Ser Arg Lys Val Asp
                245                 250                 255

Ala Leu Asp His Phe Gln Lys Cys Phe Leu Ile Leu Lys Leu His His
                260                 265                 270

Gln Arg Val Asp Ser Gly Lys Cys Ser Gln Gln Glu Gly Lys Thr Trp
                275                 280                 285

Lys Ala Ile Arg Val Asp Leu Val Met Cys Pro Tyr Glu Arg Arg Ala
290                 295                 300

Phe Ala Leu Leu Gly Trp Thr Gly Ser Ala Phe Phe Asn Arg Asp Leu
305                 310                 315                 320

Arg Arg Tyr Ala Thr His Glu Arg Lys Met Ile Leu Asp Asn His Ala
                325                 330                 335

Leu Tyr Asp Lys Thr Lys Lys Ile Phe Leu Lys Ala Glu Ser Glu Glu
                340                 345                 350

Glu Ile Phe Ala His Leu Gly Leu Asp Tyr Ile Glu Pro Trp Glu Arg
                355                 360                 365

Asn Ala
    370

<210> SEQ ID NO 30
<211> LENGTH: 370
<212> TYPE: PRT
<213> ORGANISM: ARTIFICIAL SEQUENCE
<220> FEATURE:
<223> OTHER INFORMATION: N139

<400> SEQUENCE: 30

Lys Thr Glu Ser Ala Val Lys Lys Ile Pro Leu Tyr Ala Cys Gln
1               5                   10                  15

Arg Arg Thr Thr Leu Asn Asn Phe Asn Glu Ile Phe Thr Arg Ala Phe
                20                  25                  30

Glu Val Leu Ala Glu Asn Tyr Glu Phe Lys Glu Asn Glu Ile Ser Ser
                35                  40                  45

```
Ala Thr Phe Arg Arg Ala Ala Ser Val Leu Lys Ser Leu Pro Phe Thr
         50                  55                  60

Ile Ile Ser Met Lys Asp Thr Glu Gly Ile Pro Cys Leu Gly Asp Lys
 65                  70                  75                  80

Val Lys Arg Val Ile Glu Glu Ile Ile Glu Asp Gly Glu Ser Ser Glu
                 85                  90                  95

Val Lys Ala Val Leu Asn Asp Glu Arg Tyr Gln Ala Phe Lys Leu Phe
                100                 105                 110

Thr Ser Val Phe Gly Val Gly Leu Lys Thr Ser Glu Lys Trp Phe Arg
                115                 120                 125

Met Gly Phe Arg Thr Leu Glu Lys Ile Lys Ser Asp Lys Thr Leu Lys
        130                 135                 140

Phe Thr Gln Met Gln Lys Ala Gly Phe Leu Tyr Tyr Glu Asp Leu Val
145                 150                 155                 160

Ser Gly Val Thr Arg Ala Glu Ala Glu Ala Val Gly Val Leu Val Lys
                165                 170                 175

Glu Ala Val Trp Ala Phe Leu Pro Asp Ala Phe Val Thr Met Thr Gly
                180                 185                 190

Gly Phe Arg Leu Gly Lys Lys Ile Gly His Asp Val Asp Phe Leu Ile
        195                 200                 205

Thr Ile Pro Gly Ser Thr Asp Glu Glu Glu Gln Leu Leu Pro Lys
210                 215                 220

Val Ile Asn Leu Trp Gln Arg Lys Glu Leu Leu Leu Tyr Tyr Asp Leu
225                 230                 235                 240

Val Glu Ser Thr Phe Glu Lys Leu Lys Leu Pro Ser Arg Lys Val Asp
                245                 250                 255

Ala Leu Asp His Phe Gln Lys Cys Phe Leu Ile Leu Lys Leu His His
                260                 265                 270

Gln Arg Val Asp Ser Gly Lys Cys Ser Gln Gln Glu Gly Lys Thr Trp
        275                 280                 285

Lys Ala Ile Arg Val Asp Leu Val Met Cys Pro Tyr Glu Arg Arg Ala
        290                 295                 300

Phe Ala Leu Leu Gly Trp Thr Gly Ser Ala Phe Phe Asn Arg Asp Leu
305                 310                 315                 320

Arg Arg Tyr Ala Thr His Glu Arg Lys Met Ile Leu Asp Asn His Ala
                325                 330                 335

Leu Tyr Asp Lys Thr Lys Lys Ile Phe Leu Lys Ala Glu Ser Glu Glu
                340                 345                 350

Glu Ile Phe Ala His Leu Gly Leu Asp Tyr Ile Glu Pro Trp Glu Arg
                355                 360                 365

Asn Ala
    370

<210> SEQ ID NO 31
<211> LENGTH: 370
<212> TYPE: PRT
<213> ORGANISM: ARTIFICIAL SEQUENCE
<220> FEATURE:
<223> OTHER INFORMATION: SHREW

<400> SEQUENCE: 31

Asn Val Pro Ala Pro Val Val Gln Lys Ile Ser Gln Tyr Ala Cys Gln
 1               5                  10                  15

Arg Arg Thr Thr Leu Asn Asn His Asn His Ile Phe Thr Asp Ala Phe
                 20                  25                  30
```

Glu Ile Leu Ala Glu Asn Asp Glu Phe Arg Glu Asn Glu Glu Ser Arg
          35                  40                  45

Asp Ala Phe Arg Arg Ala Ala Ser Val Leu Lys Ser Leu Pro Phe Ser
     50                  55                  60

Ile Ile Ser Met Lys Asp Thr Glu Gly Ile Pro Cys Leu Ala Asp Lys
 65                  70                  75                  80

Val Lys Arg Val Ile Glu Glu Ile Glu Asp Gly Glu Ser Ser Glu
                 85                  90                  95

Val Lys Ala Val Leu Asn Asp Glu Arg Tyr Lys Ala Phe Lys Leu Phe
             100                 105                 110

Thr Ser Val Phe Gly Val Gly Arg Lys Thr Ala Glu Lys Trp Phe Arg
             115                 120                 125

Leu Gly Phe Arg Thr Leu Glu Gly Ile Arg Asn Asp Lys Thr Leu Lys
             130                 135                 140

Leu Thr His Met Gln Lys Ala Gly Phe Leu Tyr Tyr Glu Asp Leu Val
145                 150                 155                 160

Ser Gly Val Thr Arg Ala Glu Ala Glu Ala Val Gly Val Leu Val Lys
                 165                 170                 175

Glu Ala Val Trp Ala Phe Leu Pro Asp Ala Ile Val Thr Met Thr Gly
             180                 185                 190

Gly Phe Arg Leu Gly Lys Lys Val Gly His Asp Val Asp Phe Leu Ile
             195                 200                 205

Thr Ser Pro Glu Ala Thr Glu Glu Gln Glu Gln Leu Leu His Lys
             210                 215                 220

Val Ile Thr Phe Trp Glu Lys Glu Gly Leu Leu Leu Tyr Cys Asp Leu
225                 230                 235                 240

Tyr Glu Ser Thr Phe Glu Lys Leu Lys Met Pro Ser Arg Thr Val Asp
                 245                 250                 255

Ala Leu Asp His Phe Gln Lys Cys Phe Leu Ile Leu Lys Leu His Arg
             260                 265                 270

Glu Ser Val Asp Asp Gly Thr Ser Ser Gln Leu Gln Gly Lys Thr Trp
             275                 280                 285

Lys Ala Ile Arg Val Asp Leu Val Val Cys Pro Tyr Glu Cys Arg Ala
             290                 295                 300

Phe Ala Leu Leu Gly Trp Thr Gly Ser Pro Phe Phe Asn Arg Asp Leu
305                 310                 315                 320

Arg Arg Tyr Ala Thr His Glu Arg Lys Met Met Leu Asp Asn His Ala
                 325                 330                 335

Leu Tyr Asp Lys Thr Lys Arg Lys Phe Leu Ser Ala Asp Ser Glu Glu
             340                 345                 350

Asp Ile Phe Ala His Leu Gly Leu Asp Tyr Ile Glu Pro Arg Glu Arg
             355                 360                 365

Asn Ala
   370

<210> SEQ ID NO 32
<211> LENGTH: 381
<212> TYPE: PRT
<213> ORGANISM: ARTIFICIAL SEQUENCE
<220> FEATURE:
<223> OTHER INFORMATION: M27

<400> SEQUENCE: 32

Asn Ser Ser Pro Ser Pro Val Pro Gly Ser Gln Asn Val Pro Ala Pro
 1               5                  10                  15

Val Val Lys Lys Ile Ser Gln Tyr Ala Cys Gln Arg Arg Thr Thr Leu
            20                  25                  30

Asn Asn Tyr Asn Gln Leu Phe Thr Asp Ala Leu Asp Ile Leu Ala Glu
        35                  40                  45

Asn Asp Glu Phe Arg Glu Asn Glu Ser Cys Leu Ala Phe Arg Arg
50                  55                  60

Ala Ser Ser Val Leu Lys Ser Leu Pro Phe Pro Ile Thr Ser Met Lys
65                  70                  75                  80

Asp Thr Glu Gly Ile Pro Cys Leu Gly Asp Lys Val Lys Ser Ile Ile
                85                  90                  95

Glu Gly Ile Ile Glu Asp Gly Glu Ser Ser Glu Val Lys Ala Val Leu
            100                 105                 110

Asn Asp Glu Arg Tyr Lys Ser Phe Lys Leu Phe Thr Ser Val Phe Gly
            115                 120                 125

Val Gly Leu Lys Thr Ala Glu Lys Trp Phe Arg Met Gly Phe Arg Thr
    130                 135                 140

Leu Ser Lys Ile Gln Ser Asp Lys Ser Leu Arg Phe Thr Gln Met Gln
145                 150                 155                 160

Lys Ala Gly Phe Leu Tyr Tyr Glu Asp Leu Val Ser Gly Val Asn Arg
                165                 170                 175

Pro Glu Ala Glu Ala Val Ser Met Leu Val Lys Glu Ala Val Val Thr
            180                 185                 190

Phe Leu Pro Asp Ala Leu Val Thr Met Thr Gly Gly Phe Arg Leu Gly
        195                 200                 205

Lys Met Thr Gly His Asp Val Asp Phe Leu Ile Thr Ser Pro Glu Ala
    210                 215                 220

Thr Glu Asp Glu Glu Gln Gln Leu Leu His Lys Val Thr Asp Phe Trp
225                 230                 235                 240

Lys Gln Gln Gly Leu Leu Leu Tyr Cys Asp Ile Leu Glu Ser Thr Phe
                245                 250                 255

Glu Lys Phe Lys Gln Pro Ser Arg Thr Val Asp Ala Leu Asp His Phe
            260                 265                 270

Gln Lys Cys Phe Leu Ile Leu Lys Leu Asp His Pro Arg Val His Ser
        275                 280                 285

Val Lys Ser Gly Gln Gln Glu Gly Lys Gly Trp Lys Ala Ile Arg Val
    290                 295                 300

Asp Leu Val Met Cys Pro Tyr Asp Arg Arg Ala Phe Ala Leu Leu Gly
305                 310                 315                 320

Trp Thr Gly Ser Pro Gln Phe Asn Arg Asp Leu Arg Arg Tyr Ala Thr
                325                 330                 335

His Glu Arg Lys Met Met Leu Asp Asn His Ala Leu Tyr Asp Lys Thr
            340                 345                 350

Lys Arg Val Phe Leu Glu Ala Glu Ser Glu Glu Ile Phe Ala His
        355                 360                 365

Leu Gly Leu Asp Tyr Ile Glu Pro Trp Glu Arg Asn Ala
    370                 375                 380

<210> SEQ ID NO 33
<211> LENGTH: 20
<212> TYPE: DNA
<213> ORGANISM: ARTIFICIAL SEQUENCE
<220> FEATURE:
<223> OTHER INFORMATION: PRIMER

```
<400> SEQUENCE: 33
taatacgact cactataggg                                              20

<210> SEQ ID NO 34
<211> LENGTH: 19
<212> TYPE: DNA
<213> ORGANISM: ARTIFICIAL SEQUENCE
<220> FEATURE:
<223> OTHER INFORMATION: PRIMER

<400> SEQUENCE: 34
gctagttatt gctcagcgg                                               19
```